(12) United States Patent
Reiter

(10) Patent No.: US 7,399,838 B2
(45) Date of Patent: Jul. 15, 2008

(54) SINGLE CHAIN CLASS I MAJOR HISTO-COMPATIBILITY COMPLEXES

(75) Inventor: Yoram Reiter, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 424 days.

(21) Appl. No.: 10/073,300

(22) Filed: Feb. 13, 2002

(65) Prior Publication Data

US 2003/0003535 A1    Jan. 2, 2003

Related U.S. Application Data

(63) Continuation-in-part of application No. 09/534,966, filed on Mar. 27, 2000, now abandoned.

(51) Int. Cl.
*C07K 14/74* (2006.01)
(52) U.S. Cl. .................. 530/395; 530/350; 530/402; 530/403
(58) Field of Classification Search .............. 530/350, 530/395
See application file for complete search history.

(56) References Cited

U.S. PATENT DOCUMENTS 5,635,363 A    6/1997  Altman et al.

OTHER PUBLICATIONS

Mottez, E. et al. [1995] J. Exp. Med. 181:493-502.*
Lone, YC et al. J. Immunotherapy [1998] 21(4):283-294.*
Ojcius et al, "Dissociation of the Peptide-MHC Class I Complex Limits the Binding Rate of Exogenous Peptide", *J. Immunology*, 151(11):6020-6026, 1993.
Parker et al, "Sequence motifs important for peptide binding to the human MHC class I molecule, HLA-A2", *J Immunol.*, 149(11):3580-7, 1992.
Lone et al, "In vitro induction of specific cytotoxic T lymphocytes using recombinant single-chain MHC class I/peptide complexes", *J Immunother.*, 21(4):283-94,1998.
Lee et al, "Functional cell surface expression by a recombinant single-chain class I major histocompatibility complex molecule with a cis-active beta 2-microglobulin domain", *Eur J Immunol.*, 24(11):2633-9, 1994.
Kourilsky et al, "Immunological Issues in Vaccine Trials: T-Cell Responses", found in "Preclinical and Clinical Development of New Vaccines", Plotkin et al (eds), Karger, Basel, vol. 95, pp. 117-124, 1998.

* cited by examiner

*Primary Examiner*—Eileen B. O'Hara
*Assistant Examiner*—F. Pierre VanderVegt

(57) ABSTRACT

A recombinant polypeptide and nucleic acid constructs capable of expressing the recombinant polypeptide are provided. The recombinant polypeptide comprises a chimeric polypeptide including an antigenic peptide being capable of binding a human MHC class I, a functional human β-2 microglobulin and a functional human MHC class I heavy chain.

4 Claims, 14 Drawing Sheets

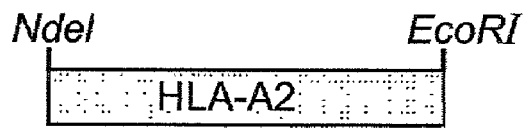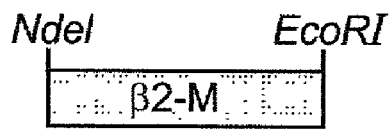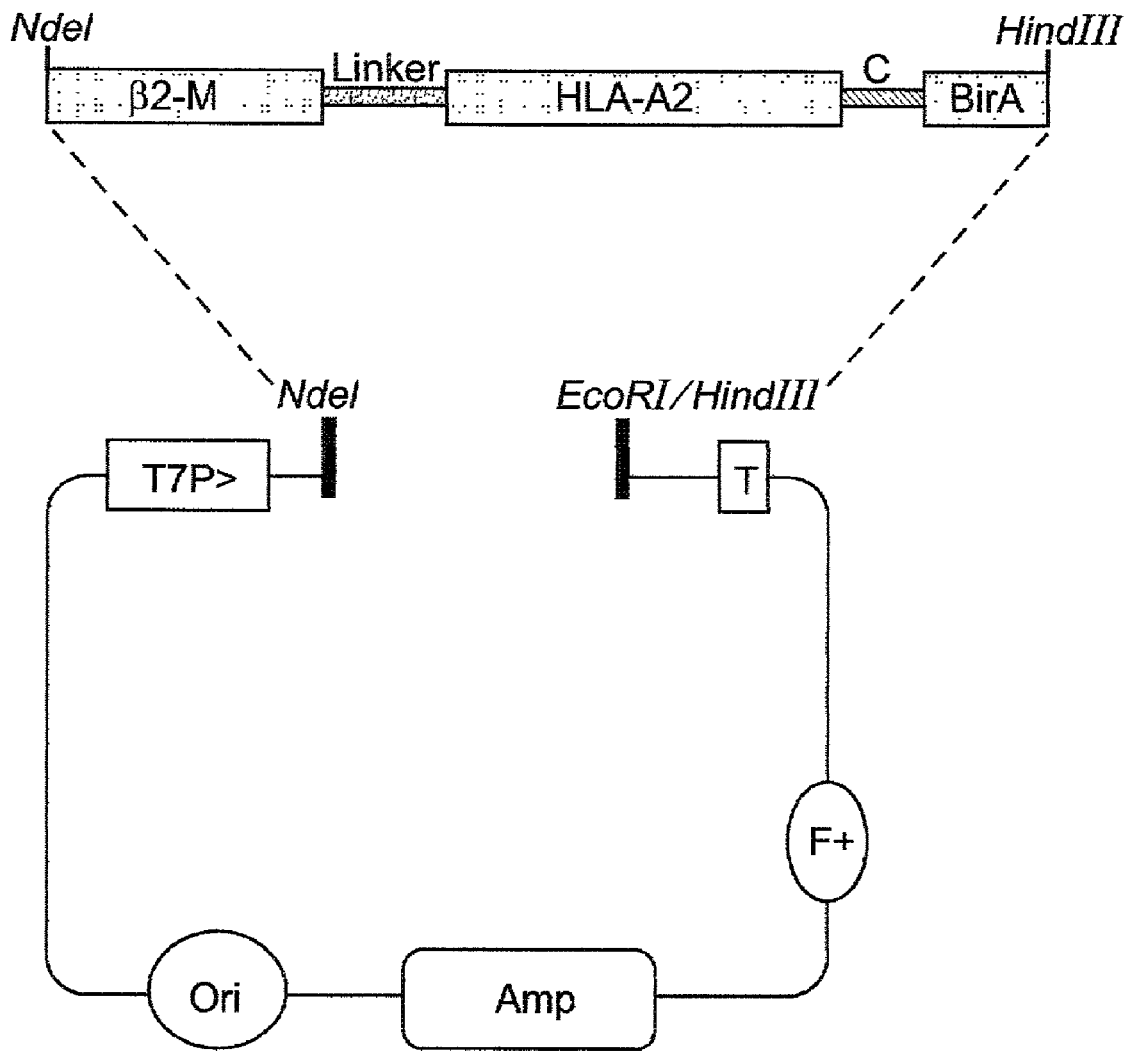
Fig. 1

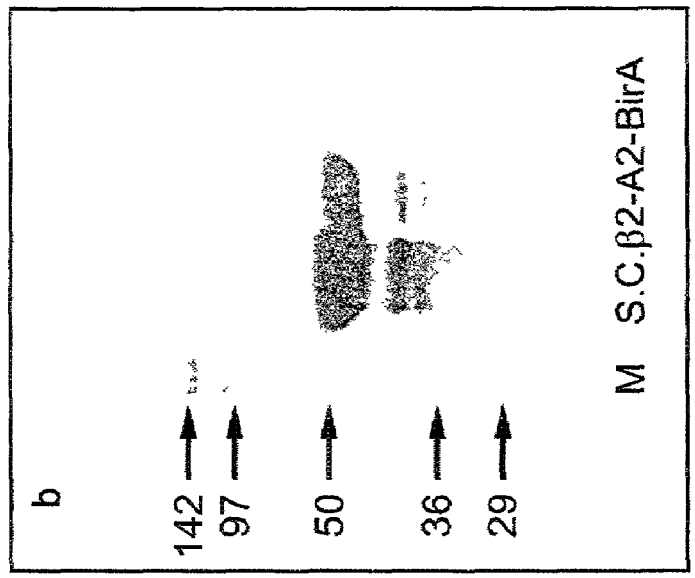
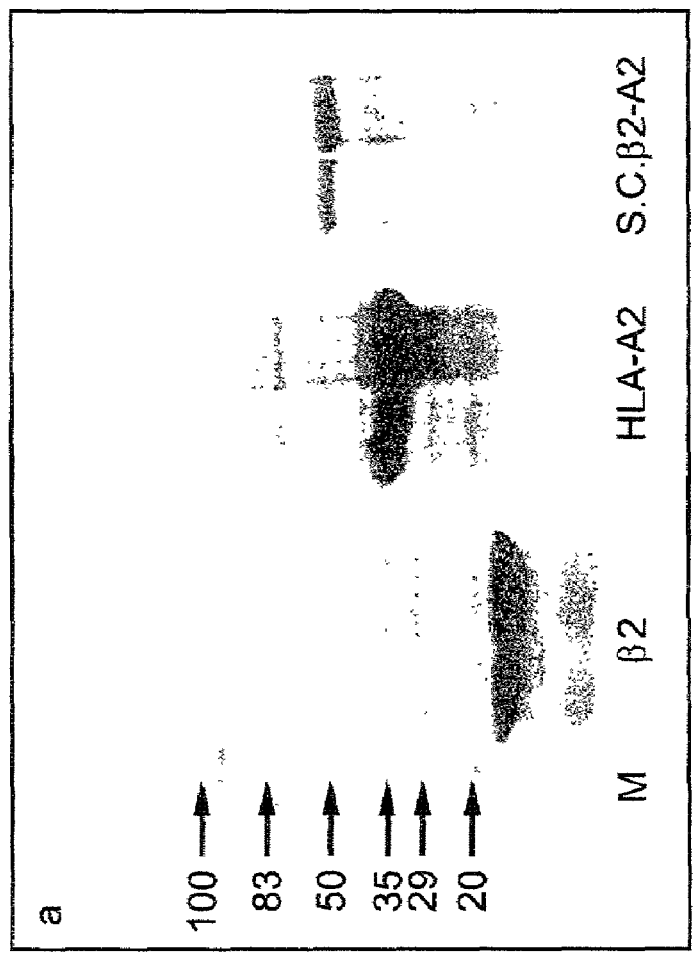
Fig. 2a
Fig. 2b

ScMHC-BirA/209

ScMHC-BirA-Biotin/209

ScMHC-BirA-Biotin/209

10 μg/ml

1 μg/ml 0.05 μg/ml

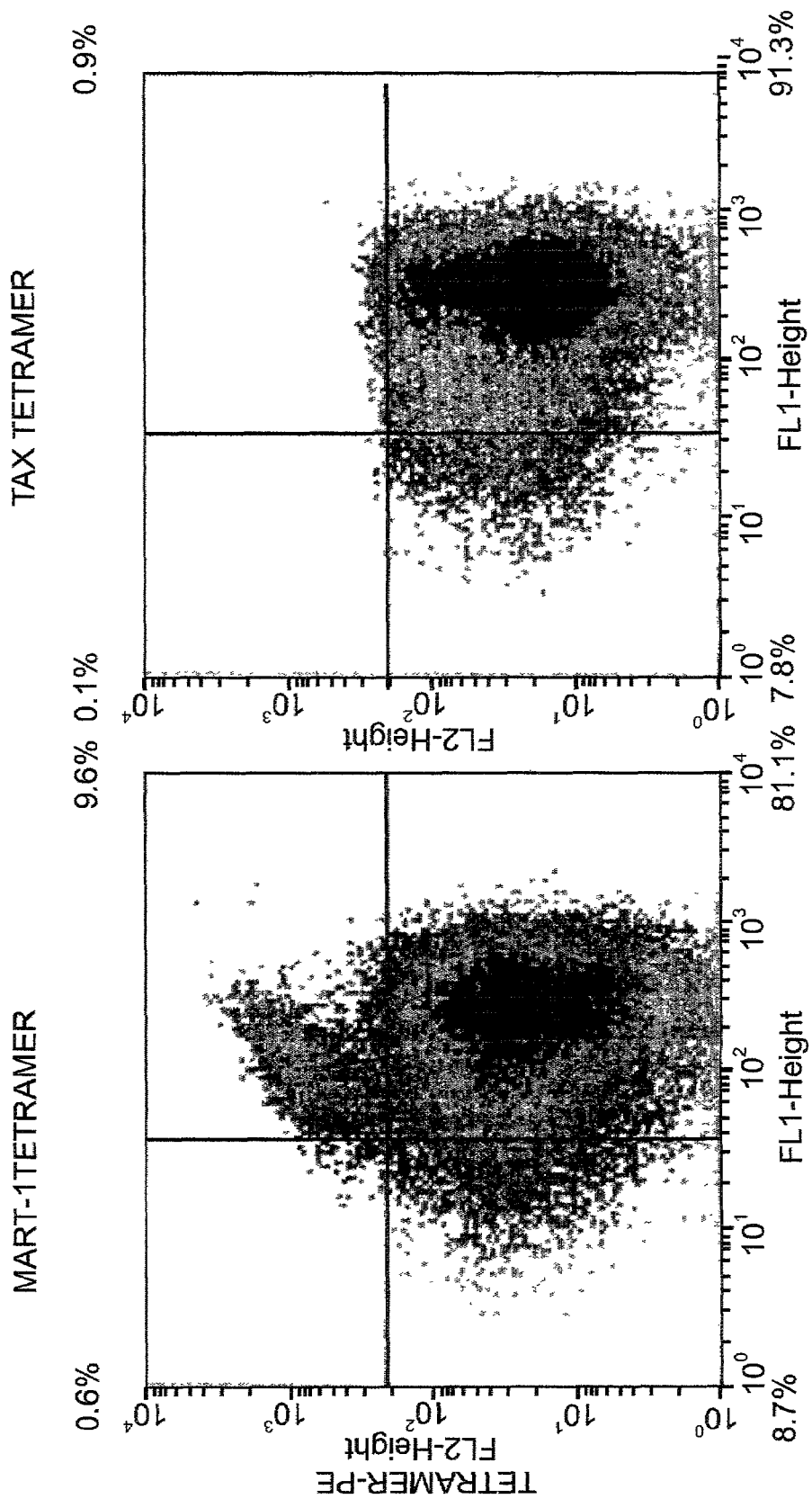

```
                         SEQUENCE LISTING

<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Ile Met Asp Gln Val Pro Phe Ser Val
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Tyr Leu Glu Pro Gly Pro Val Thr Val
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Leu Leu Phe Gly Tyr Pro Val Tyr Val
1               5

<210> SEQ ID NO 4
<211> LENGTH: 1048
<212> TYPE: DNA
```

<213> ORGANISM: Homo sapiens

<400> SEQUENCE: 4

```
atgatccagc gtactccaaa gattcaggtt tactcacgtc atccagcaga gaatggaaag      60
tcaaatttcc tgaattgcta tgtgtctggg tttcatccat ccgacattga agttgactta     120
ctgaagaatg gagagagaat tgaaaaagtg gagcattcag acttgtcttt cagcaaggac     180
tggtctttct atctcttgta ttatactgag ttcaccccca ctgaaaaaga tgagtatgcc     240
tgccgtgtga accacgtgac tttgtcacag cccaagatag ttaagtggga tcgagacatg     300
ggtggcggtg gaagcggcgg tggaggctct ggtggaggtg cagcggctc tcactccatg      360
aggtatttct tcacatccgt gtcccggccc ggccgcgggg agccccgctt catcgcagtg     420
ggctacgtgg acgacacgca gttcgtgcgg ttcgacagcg acgccgcgag ccagaggatg     480
gagccgcggg cgccgtggat agagcaggag ggtccggagt attgggacgg ggagacacgg     540
aaagtgaagg cccactcaca gactcaccga gtggacctgg gaccctgcg cggctactac      600
aaccagagcg aggccggttc tcacaccgtc cagaggatgt atggctgcga cgtggggtcg     660
gactggcgct cctccgcgg gtaccaccag tacgcctacg acggcaagga ttacatcgcc      720
ctgaaagagg acctgcgctc ttggaccgcg gcggacatgg cagctcagac caccaagcac     780
aagtgggagg cggcccatgt ggcggagcag ttgagagcct acctggaggg cacgtgcgtg     840
gagtggctcc gcagatacct ggagaacggg aaggagacgc tgcagcgcac ggacgccccc     900
aaaacgcaca tgactcacca cgctgtctct gaccatgaag ccaccctgag gtgctgggcc     960
ctgagcttct accctgcgga gatcacactg acctggcagc ggacttggag gaatctttga    1020
ggcaatgaag atggagctgc gggactga                                       1048
```

<210> SEQ ID NO 5
<211> LENGTH: 415
<212> TYPE: PRT
<213> ORGANISM: Artificial Sequence
<220> FEATURE:
<223> OTHER INFORMATION: human beta2 microglobulin linked to MHC class I heavy chain

<400> SEQUENCE: 5

```
Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met Gly Gly Gly Gly Ser Gly Gly Gly Gly Ser Gly Gly
            100                 105                 110

Gly Gly Ser Gly Ser His Ser Met Arg Tyr Phe Phe Thr Ser Val Ser
        115                 120                 125

Arg Pro Gly Arg Gly Glu Pro Arg Phe Ile Ala Val Gly Tyr Val Asp
    130                 135                 140

Asp Thr Gln Phe Val Arg Phe Asp Ser Asp Ala Ala Ser Gln Arg Met
```

```
                145                 150                 155                 160
Glu Pro Arg Ala Pro Trp Ile Glu Gln Glu Gly Pro Glu Tyr Trp Asp
                165                 170                 175

Gly Glu Thr Arg Lys Val Lys Ala His Ser Gln Thr His Arg Val Asp
            180                 185                 190

Leu Gly Thr Leu Arg Gly Tyr Tyr Asn Gln Ser Glu Ala Gly Ser His
        195                 200                 205

Thr Val Gln Arg Met Tyr Gly Cys Asp Val Gly Ser Asp Trp Arg Phe
    210                 215                 220

Leu Arg Gly Tyr His Gln Tyr Ala Tyr Asp Gly Lys Asp Tyr Ile Ala
225                 230                 235                 240

Leu Lys Glu Asp Leu Arg Ser Trp Thr Ala Ala Asp Met Ala Ala Gln
                245                 250                 255

Thr Thr Lys His Lys Trp Glu Ala Ala His Val Ala Glu Gln Leu Arg
            260                 265                 270

Ala Tyr Leu Glu Gly Thr Cys Val Glu Trp Leu Arg Arg Tyr Leu Glu
        275                 280                 285

Asn Gly Lys Glu Thr Leu Gln Arg Thr Asp Ala Pro Lys Thr His Met
    290                 295                 300

Thr His His Ala Val Ser Asp His Glu Ala Thr Leu Arg Cys Trp Ala
305                 310                 315                 320

Leu Ser Phe Tyr Pro Ala Glu Ile Thr Leu Thr Trp Gln Arg Asp Gly
                325                 330                 335

Glu Asp Gln Thr Gln Asp Thr Glu Leu Val Glu Thr Arg Pro Ala Gly
            340                 345                 350

Asp Gly Thr Phe Gln Lys Trp Ala Ala Val Val Val Pro Ser Gly Gln
        355                 360                 365

Glu Gln Arg Tyr Thr Cys His Val Gln His Glu Gly Leu Pro Lys Pro
    370                 375                 380

Leu Thr Leu Arg Trp Glu Gln Ser Thr Arg Gly Gly Ala Ser Gly Gly
385                 390                 395                 400

Gly Leu Gly Gly Ile Phe Glu Ala Met Lys Met Glu Leu Arg Asp
                405                 410                 415

<210> SEQ ID NO 6
<211> LENGTH: 280
<212> TYPE: PRT
<213> ORGANISM: Homo sapiens

<400> SEQUENCE: 6

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Ser Asp Trp Arg Phe Leu Arg Gly
            100                 105                 110
```

```
Tyr His Gln Tyr Ala Tyr Asp Gly Lys Asp Tyr Ile Ala Leu Lys Glu
        115                 120                 125

Asp Leu Arg Ser Trp Thr Ala Asp Met Ala Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Gln Ser Thr Arg Gly
        275                 280

<210> SEQ ID NO 7
<211> LENGTH: 100
<212> TYPE: PRT
<213> ORGANISM: Homo sapiens

<400> SEQUENCE: 7

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met
            100

<210> SEQ ID NO 8
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 8
aggagatata catatgggct ctcactccat gaggta                              36

<210> SEQ ID NO 9
<211> LENGTH: 43
<212> TYPE: DNA
<213> ORGANISM: Artificial Sequence
```

```
<220> FEATURE:
<223> OTHER INFORMATION: synthetic oligonucleotide

<400> SEQUENCE: 9
cgggctttgt tagcaccgat tcataggtga ggggcttggg caa                    43

<210> SEQ ID NO 10
<211> LENGTH: 15
<212> TYPE: PRT
<213> ORGANISM: Artificial Sequence
<220> FEATURE:
<223> OTHER INFORMATION: linker peptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 11
ggagatatac atatgatcca gcgtactcca aagat                             35

<210> SEQ ID NO 12
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 12
cgggctttgt tagcagccga attcattaca tgtctcgatc ccacttaac              49

<210> SEQ ID NO 13
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 13
ggaaggcgtt ggcgcatatg atccagcgta ctccaaagat t                      41

<210> SEQ ID NO 14
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 14
ggaagcggcg gtggaggctc tggtggaggt ggcagcggct ctcactccat             50

<210> SEQ ID NO 15
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 15
ggaagcggcg gtggaggctc tggtggaggt ggcagcggct ctcactccat             50
```

```
<210> SEQ ID NO 16
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 16
gggagaattc ttactcccat ctcagggtga ggggcttggg caa            43

<210> SEQ ID NO 17
<211> LENGTH: 14
<212> TYPE: PRT
<213> ORGANISM: Artificial Sequence
<220> FEATURE:
<223> OTHER INFORMATION: specific biotinylation peptide sequence

<400> SEQUENCE: 17

Leu Gly Gly Ile Phe Glu Ala Met Lys Met Glu Leu Arg Asp
1               5                   10

<210> SEQ ID NO 18
<211> LENGTH: 11
<212> TYPE: PRT
<213> ORGANISM: Artificial Sequence
<220> FEATURE:
<223> OTHER INFORMATION: linker

<400> SEQUENCE: 18

Gln Ser Thr Arg Gly Gly Ala Ser Gly Gly Gly
1               5                   10

<210> SEQ ID NO 19
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 19
cagtaaaagc tttttatcag cctccgaact gtggatgcct ccacgccgaa cctccaccag    60
aaccacctcc ggacccgcca cctccctccc atctcagggt                         100

<210> SEQ ID NO 20
<211> LENGTH: 39
<212> TYPE: DNA
<213> ORGANISM: Artificial Sequence
<220> FEATURE:
<223> OTHER INFORMATION: BirA recognition tag sequence

<400> SEQUENCE: 20
ggaatctttg aggcaatgaa gatggagctg cgggactga                 39
```

SINGLE CHAIN CLASS I MAJOR HISTO-COMPATIBILITY COMPLEXES

This is a Continuation-In-Part of U.S. patent application Ser. No. 09/534,966, filed Mar. 27, 2000.

FIELD AND BACKGROUND OF THE INVENTION

The present invention relates to methods of generating a functional mammalian single chain MHC class I complex in prokaryotic expression systems and a functional human single chain MHC class I complex in eukaryotic or prokaryotic expression systems, which complexes are capable of presenting specific antigenic peptides restricted to class I MHC and recognizable by specific CTL clones or CD+8 T-cells. The present invention further relates to a method of generating a functional mammalian single chain MHC class I-peptide complex in eukaryotic, or preferably prokaryotic expression systems, to nucleic acid constructs encoding said single chain MHC class I complexes and to a novel human single chain MHC class I polypeptide.

The major histocompatibility complex (MHC) is a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

Major histocompatibility complex (MHC) class I molecules are expressed on the surface of nearly all cells. These molecules function in presenting peptides which are mainly derived from endogenously synthesized proteins to CD8+ T cells via an interaction with the $\alpha\beta$ T-cell receptor [1-4]. The class I MHC molecule is a heterodimer composed of a 46-kDa heavy chain which is non-covalently associated with the 12-kDa light chain $\beta$-2 microglobulin. Class I MHC-restricted peptides, which are typically 8-10-amino acid-long, bind to the heavy chain $\alpha 1$-$\alpha 2$ groove via two or three anchor residues that interact with corresponding binding pockets in the MHC molecule. The $\beta$-2 microglobulin chain plays an important role in MHC class I intracellular transport, peptide binding, and conformational stability [5]. For most class I molecules, the formation of a heterodimer consisting of the MHC class I heavy chain, peptide (self or antigenic) and $\beta$-2 microglobulin is required for biosynthetic maturation and cell-surface expression [5].

Research studies performed on peptide binding to class I MHC molecules enable to define specific MHC motifs functional in displaying peptides derived from viral or tumor antigens that are potentially immunogenic and might elicit specific response from cytotoxic T lymphocytes (CTLs) [6,7].

The realization that CTLs have an important role in the control of many diseases, including chronic viral diseases, such as AIDS, and cancer have lead to an increased need to produce sufficient amounts of stable class I MHC complexes for functional and structural studies.

Soluble MHC molecules bound to various peptides are a valuable tool for the study of disease-related immune responses, for characterizing MHC-T-cell receptor (TCR) interactions [6], for structural studies [4], and more recently for direct visualization of antigen-specific T cells [8]. These molecules can be also used to activate specific CTLs in vitro as well as to study their phenotypic characteristics.

In recent years, various approaches have been used in attempts to develop an in vitro protocol for the induction of cytotoxic T cell responses against viral and tumor antigens [9-10]. To effectively activate T-cells, a high density of MHC-peptide complexes on the surface of the antigen presenting cells must be utilized [7-10]. Thus, a desirable approach for in-vitro T-cell activation would be to use soluble MHC-peptide complexes.

To overcome the low affinity binding of TCRs to soluble MHC molecules and as such to provide efficient T-cell activation, multimerization of the MHC-peptide complexes must be effected.

Soluble MHC multimers posses a higher avidity for T-cells since they provide multi-point binding of TCRs with their MHC-peptide ligands. As such, multimeric forms (tetramers) of MHC-peptide complexes have been the center of much interest recently, because they can be used for direct phenotypic characterization of T cell responses in normal as well as pathological conditions, thus, providing insight into the pathophysiology and mechanisms of various diseases.

However, such studies require a reproducible method for producing large amounts of soluble and functional multimeric MHC-peptide complexes. Thus, attempts were made to produce recombinant MHC class I and class II complexes [11-23] which are soluble and which can be produced in large quantities.

Early studies utilizing recombinant techniques, separately expressed the heavy chain and $\beta$-2 microglobulin components of the MHC complex in *E. Coli* and subsequently refolded them in-vitro in the presence of an antigenic peptide [11].

More recently, recombinant MHC complexes were expressed in eukaryotic expression systems and secreted therefrom in the form of a single polypeptide which included the heavy chain covalently linked to the $\beta$-2 microglobulin chain thus forming a stable and functional MHC complex which can be subsequently bound to a peptide of interest [12-15, 19, 21-23]. The expression of functional MHC complexes in eukaryotic cells suffers from several inherent limitations. Since the expressed polypeptides form a functional MHC complex they bind peptides endogenously derived from the cells utilized for expression and as such the purified MHC complex must be subjected to a peptide exchange step following purification [13]. In addition, the production yields of these single-chain MHC-peptide complexes was limited, typically reaching levels of several hundred micrograms per liter of culture supernatant.

The present invention provides a novel approach for the production of unprecedented large amounts of soluble, stable and functional MHC-peptide complex by utilizing high level bacterial expression of a single-chain MHC class I polypeptide or co-expression of the single chain MHC class I polypeptide and an MHC class I restricted antigenic peptide followed by in-vitro reconstitution of the scMHC class I-peptide complex via redox-shuffling and refolding in the presence of the antigenic peptide.

The present invention further provides a novel human single chain MHC class I polypeptide which is functional and which can therefore be utilized in either the monomeric or preferably the multimeric form to present MHC class I restricted antigenic peptides to CTL clones or to CD8+ T-cells from various sources.

SUMMARY OF THE INVENTION

According to one aspect of the present invention there is provided a nucleic acid construct comprising a first nucleic acid sequence including a first polynucleotide encoding a functional human β-microglobulin, being translationally fused upstream of a second polynucleotide encoding a functional human MHC class I heavy chain.

According to further features in preferred embodiments of the invention described below, the nucleic acid construct further comprising a second nucleic acid sequence encoding an antigenic peptide, the antigenic peptide being capable of binding a human MHC class I complex.

According to still further features in the described preferred embodiments the second polynucleotide encodes α1-3 domains of the human MHC class I heavy chain.

According to another aspect of the present invention there is provided a nucleic acid construct comprising (a) a first nucleic acid sequence including (i) a first polynucleotide encoding a functional mammalian β-2 microglobulin; and (ii) a second polynucleotide encoding a functional mammalian MHC class I heavy chain, the second polynucleotide being translationally fused downstream of the first polynucleotide; and (b) a cis acting regulatory sequence being selected capable for directing expression of the first nucleic acid sequence in bacteria.

According to still further features in the described preferred embodiments the cis acting regulatory sequence is selected from the group consisting of a bacterial derived cis acting regulatory sequence and a phage derived cis acting regulatory sequence.

According to still another aspect of the present invention there is provided a transformed cell comprising any of the nucleic acid constructs described herein. The cell can be a eukaryotic cell, such as, for example, a mammalian cell, an insect cell, a plant cell, a yeast cell and a protozoa cell, or alternatively, the cell can be a bacterial cell.

According to still another aspect of the present invention there is provided a host cell being co-transformed with (a) a first expression construct including a first polynucleotide encoding a functional mammalian β-2 microglobulin, being translationally fused upstream of a second polynucleotide encoding a functional MHC class I heavy chain; and (b) a second expression construct including a third polynucleotide encoding an antigenic peptide, wherein when the first, second and third polynucleotides are co-expressed in the host cell, an MHC class I-antigenic peptide complex is formed.

According to still further features in the described preferred embodiments the first nucleic acid sequence further includes an in-frame linker polynucleotide encoding a linker peptide interposed between the first and the second polynucleotides.

According to still further features in the described preferred embodiments the first nucleic acid sequence further includes an in-frame tag sequence encoding a peptide capable of being enzymatically modified to include a binding entity.

According to still further features in the described preferred embodiments the linker peptide is as set forth in SEQ ID NO:10.

According to still further features in the described preferred embodiments the nucleic acid construct further comprising a first cis acting regulatory sequence for regulating expression of the first nucleic acid sequence.

According to still further features in the described preferred embodiments the nucleic acid construct further comprising a second cis acting regulatory sequence for regulating expression of the second nucleic acid sequence.

According to still further features in the described preferred embodiments the cis acting regulatory sequence is functional in a bacterial host.

According to still another aspect of the present invention there is provided a recombinant polypeptide comprising an amino acid sequence including a functional human β-2 microglobulin directly or indirectly covalently linked to a functional human MHC class I heavy chain.

According to still further features in the described preferred embodiments the recombinant polypeptide further comprising a linker peptide being interposed between the functional human β-2 microglobulin and the functional human MHC class I heavy chain. Preferably, the recombinant polypeptide comprising an amino acid sequence as set forth in SEQ ID NO:5.

According to yet another aspect of the present invention there is provided a preparation of bacterial derived inclusion bodies comprising over 30 percent by weight of a recombinant polypeptide including an amino acid sequence including a functional mammalian β-2 microglobulin directly or indirectly covalently linked to a functional mammalian MHC class I heavy chain.

According to an additional aspect of the present invention there is provided a method of producing a functional MHC class I molecule comprising the steps of (a) expressing, in bacteria, a single chain MHC class I polypeptide including a functional mammalian β-2 microglobulin amino acid sequence directly or indirectly covalently linked to a functional mammalian MHC class I heavy chain amino acid sequence; and (b) isolating the single chain MHC class I polypeptide.

According to still further features in the described preferred embodiments the method further comprising the step of (c) refolding the single chain MHC class I polypeptide in presence of an antigenic peptide capable of binding the single chain MHC class I polypeptide, to thereby generate an MHC class I-antigenic peptide complex.

According to still further features in the described preferred embodiments the method further comprising the step of (d) isolating the MHC class I-antigenic peptide complex via size exclusion chromatography.

According to still further features in the described preferred embodiments the antigenic peptide is co-expressed along with the single chain MHC class I polypeptide in the bacteria.

According to still further features in the described preferred embodiments step (a) is effected such that the single chain MHC class I polypeptide forms inclusion bodies in the bacteria. According to still further features in the described preferred embodiments the antigenic peptide and the single chain MHC class I polypeptide form inclusion bodies in the bacteria.

According to still further features in the described preferred embodiments the step of isolating the polypeptide further includes the steps of (i) denaturing the inclusion bodies so as to release protein molecules therefrom; and (ii) renaturing the protein molecules.

According to still further features in the described preferred embodiments the step of renaturing the protein molecules is effected in the presence of an antigenic peptide capable of binding the single chain MHC class I polypeptide.

According to still further features in the described preferred embodiments the antigenic peptide is co-expressed along with the single chain MHC class I polypeptide in the bacteria.

According to still further features in the described preferred embodiments the mammalian β-2 microglobulin amino acid sequence is a human β-2 microglobulin amino acid sequence and further wherein the mammalian MHC class I heavy chain amino acid sequence is a human MHC class I heavy chain amino acid sequence.

According to still another aspect of the present invention, there is provided a multimeric MHC class I complex comprising a plurality of recombinant polypeptide monomers each including a functional human β-2 microglobulin directly or indirectly covalently linked to a functional human MHC class I heavy chain.

According to still further features in the described preferred embodiments the plurality of recombinant polypeptide monomers are linked to a common substrate.

According to yet another aspect of the present invention there is provided a chimeric polypeptide comprising an antigenic peptide being capable of binding a human MHC class I, a functional human β-2 microglobulin and a functional human MHC class I heavy chain.

According to still further features in the described preferred embodiments the chimeric polypeptide further comprising a linker peptide being interposed between the functional human β-2 microglobulin and the functional human MHC class I heavy chain.

According to still further features in the described preferred embodiments the chimeric polypeptide further comprising a linker peptide being interposed between the antigenic peptide and the functional human β-2 microglobulin.

According to still another aspect of the present invention there is provided a nucleic acid construct comprising a nucleic acid sequence encoding a chimeric polypeptide including an antigenic peptide being capable of binding a human MHC class I, a functional human β-2 microglobulin and a functional human MHC class I heavy chain.

According to still further features in the described preferred embodiments the chimeric polypeptide further includes a linker peptide interposed between the antigenic peptide and the functional human β-2 microglobulin.

According to still further features in the described preferred embodiments the chimeric polypeptide further includes a linker peptide interposed between the functional human β-2 microglobulin and the functional human MHC class I heavy chain.

According to still further features in the described preferred embodiments the linker peptide is as set forth in SEQ ID NO:10.

According to still further features in the described preferred embodiments the chimeric polypeptide further includes a peptide capable of being enzymatically modified to include a binding entity.

According to still further features in the described preferred embodiments the nucleic acid construct further comprising a cis acting regulatory sequence for regulating expression of the nucleic acid sequence.

According to still further features in the described preferred embodiments the cis acting regulatory sequence is functional in a bacterial host.

According to still further features in the described preferred embodiments there is provided a transformed cell comprising the nucleic acid construct described above.

The present invention successfully addresses the shortcomings of the presently known configurations by providing a method of generating large quantities of pure single chain MHC class I polypeptides which can be utilized in monomeric or multimeric form to present antigenic peptides to CTL clones. The present invention further addresses the shortcomings of the presently known configurations by providing, for the first time, a human single chain MHC class I polypeptide functional in both monomeric and multimeric form in presenting antigenic peptides to CTL clones.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates the various expression cassettes of the present invention which were cloned into a bacterial expression vector. β2-M—human β-2 microglobulin, HLA-A2—human MHC class I heavy chain, BirA—a sequence encoding a peptide including a biotin protein ligase-Bir A enzyme recognition sequence.

FIGS. 2a-b are SDS page gels depicting the analysis of the expression products of the various constructs of FIG. 1. The β-2 microglobulin, HLA-A2, and the scMHC polypeptides were expressed in E. Coli BL21 cells and the polypeptides accumulated as insoluble inclusion bodies. Inclusion bodies were purified and analyzed by reduced SDS-PAGE electrophoresis on 10% gels. β-2—human β-2 microglobulin, HLA-A2—human MHC class I heavy, S.C. β-2-A2—human scMHC class I and S.C. β2-A2-BirA human scMHC-BirA. Arrows indicate molecular size markers. In all cases, the recombinant polypeptide expressed comprised >90% of total inclusion body protein.

FIG. 6a depicts mass spectrometry analysis of eluted peptides, wherein FIGS. 6b-c depict mass estimation of the proteins.

FIG. 7a depicts the ability of various scMHC-peptide complexes coated onto microtiter plates to activate the G9-209-2M specific CTL clone R6C12. Spontaneous release (Spont) was determined by incubation of CTLs in wells that were not coated with the various complexes. FIG. 7b depicts the role of peptide specificity in CTL activation. scMHC tetramers complexed with the G9-209-2M peptide were generated as described in the Examples section. The soluble tetramers were incubated with the 209-specific CTL clone R6C12 or with the Mart-1-specific clone JB2F4 as indicated. Spontaneous IFNg release was determined by incubating the CTL clones with the unbiotinylated scMHC-peptide complex (which does not support tetramer formation). FIG. 7c depicts the dependency of CTLs activation on tetramer formation. The 209-specific CTL clone R6C12 was incubated with various biotinylated or unbiotinylated scMHC-BirA-peptide complexes and streptavidin. Spontaneous release was determined by incubating CTLs with the scMHC-209 complex which does not contain the BirA tag.

FIGS. 9a-b are FACS analysis images of CTL clones specific for the MART-1 peptide 27-35 incubated with either scMHC-BirA/MART-1 PE-labeled tetramers (FIG. 9a) or with scMHC-BirA/TAX PE-labeled tetramers (FIG. 9b) and co-stained with FITC-labeled anti CD8 antibody. Specific staining of high avidity CTLs was observed only when using the specific and functional MART-1 peptide-containing scMHC tetramer.

FIG. 10a is the FACS image of T-cells from non-immunized mice stained with scMHC-BirA/TAX tetramer and FIG. 10b is the FACS image of T-cells from TAX-immunized mice stained with the tetramers. Both preparations were also double stained with anti-CD8.

DESCRIPTION OF THE PREFERRED EMBODIMENTS

Figures 3A, 3B, 3C:
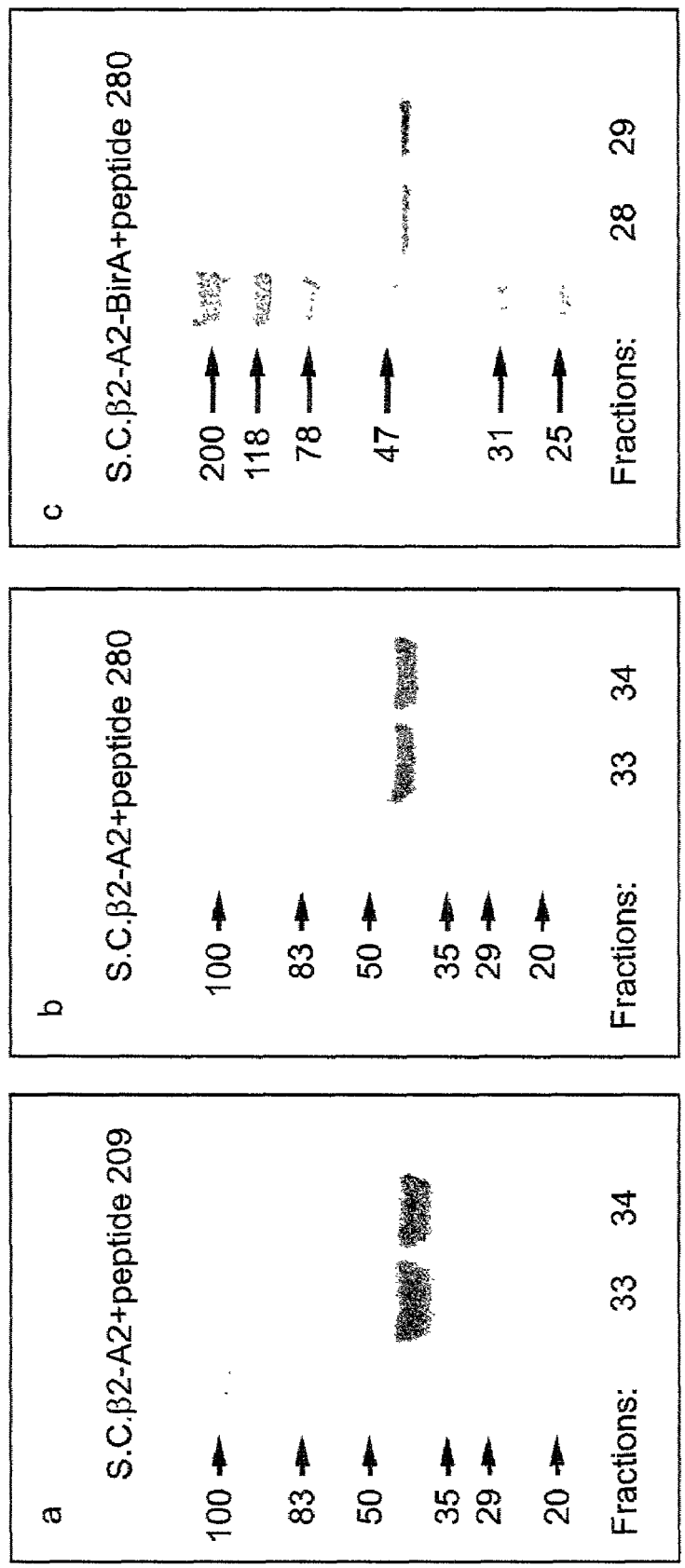
FIGS. 3a-c are SDS-PAGE gels depicting the analysis of refolded purified single-chain MHC-peptide complexes. scMHC-peptide complexes were generated by refolding of purified solubilized inclusion bodies in the presence of antigenic peptides as described in the Examples section. The refolded complexes were further purified by size-exclusion chromatography and fractions were analyzed by non-reduced SDS-PAGE on 10% gels. depicted are representative fractions of the scMHC complexed with the G9-209-2M (FIG. 3a) and G9-280-9V (FIG. 3b) gp100-derived peptides and the scMHC-BirA-complexed with the G9-280-9V peptide (FIG. 3c).

The present invention is of methods of generating a functional mammalian single chain MHC class I complex in prokaryotic expression systems and a functional human single chain MHC class I complex in eukaryotic or prokaryotic expression systems, which complexes are capable of presenting specific antigenic peptides restricted to specific CTL clones. The present invention is further of a method of generating a functional mammalian single chain MHC class I-peptide complex in eukaryotic, or preferably prokaryotic expression systems. The present invention is also of nucleic acid constructs encoding said single chain MHC class I complexes and of a novel human single chain MHC class I polypeptide.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following description or illustrated in the drawings described in the Examples section. The invention is capable of other embodiments or of being practiced or carried out in various ways. Also, it is to be understood that the phraseology and terminology employed herein is for the purpose of description and should not be regarded as limiting.

Soluble class I MHC-peptide complexes are invaluable reagents for characterizing immune responses involving CTLs, for measuring the affinity of MHC-TCR interactions, and for visualization of antigen-specific T cells.

One of the limitations in generating and using recombinant MHC-peptide complexes is a relatively low production efficiency. Most of the present studies utilize production methods that are based on transfection of cells with MHC constructs which express and secrete either scMHC or complexed MHC to the cell culture medium [12-23]. These complexes contain peptides from endogenously-expressed proteins which have to be subsequently exchanged with the desired peptide to be displayed in the complex [13].

Alternative methods for efficiently producing recombinant MHC-peptide complexes is by expression of the heavy chain and β-2 microglobulin separately in *E. Coli.* followed by co-refolding in vitro in the presence of antigenic peptide [8, 11]. Although such methods present some advantages as compared to the eukaryotic methods described above, the quantity and purity of the MHC complex produced thereby still fall well below of that required for various studies.

While reducing the present invention to practice, it was uncovered that recombinant single chain (sc) MHC-peptide complexes produced in *E. Coli* constitute an efficient new way for the generation of unprecedented large amounts (e.g., grams) of highly purified and functional MHC-peptide complexes, as well as MHC-peptide tetramers.

As is further described in the Examples section that follows human scMHC-peptide complexes generated from *E. Coli* inclusion bodies by in vitro refolding in the presence of antigenic peptides are highly pure and functional.

Thus, according to one aspect of the present invention there is provided a nucleic acid construct which includes a first nucleic acid sequence including a first polynucleotide encoding a functional human β-2 microglobulin translationally fused upstream of a second polynucleotide encoding a functional human MHC class I heavy chain.

As used herein the term "functional" when used in reference to the β-2 microglobulin and heavy chain polypeptides regions of a single chain MHC class I complex refers to any portion of each which is capable of contributing to the assembly of a functional single chain MHC class I complex (i.e., capable of binding and presenting to CTLs specific antigenic peptides when complexed).

Preferably, the first polynucleotide encodes the entire β-2 microglobulin polypeptide while the second polynucleotide encodes the α1-3 domains of the heavy chain.

The phrases "translationally fused" and "in frame" are interchangeably used herein to refer to polynucleotides which are covalently linked to form a single continuous open reading frame spanning the length of the coding sequences of the linked polynucleotides. Such polynucleotides can be covalently linked directly or preferably indirectly through a spacer or linker region.

Thus, according to a preferred embodiment of the present invention, the nucleic acid sequence further includes an in-frame linker polynucleotide. This linker polynucleotide encodes a linker peptide and is interposed between the first and said second polynucleotides.

The linker peptide is selected of an amino acid sequence which is inherently flexible, such that the polypeptides encoded by the first and said second polynucleotides independently and natively fold following expression thereof, thus facilitating the formation of a functional single chain (sc) human MHC class I complex.

According to another preferred embodiment of the present invention the linker peptide is as set forth in SEQ ID NO:10.

Thus, the first nucleic acid sequence of this aspect of the present invention, encodes a functional human single chain MHC class I polypeptide. Preferably, the first nucleic acid sequence is as set forth in SEQ ID NO: 4.

According to another preferred embodiment of the present invention, the first nucleic acid sequence further includes an in-frame tag sequence (such as that set forth in SEQ ID NO:20) which encodes a Is peptide capable of being enzymatically modified to include a binding entity. As is further described in the Examples section that follows, the binding entity, which can be, for example, biotin, can be utilized by the present invention to assemble a plurality of scMHC class I polypeptides into multimers, by providing a ligand, such as avidin or streptavidin which serves as a common attachment entity for the scMHC class I polypeptides. MHC class I multimers are particularly advantageous for peptide mediated CTL activation as is further described in the Examples section which follows.

According to another preferred embodiment of the present invention the nucleic acid construct further includes a first cis acting regulatory sequence. The cis acting regulatory sequence can include a promoter sequence and additional transcriptional or a translational enhancer sequences all of which serve for facilitating the expression of the nucleic acid sequence when introduced into a host cell. Specific examples of promoters are described hereinbelow in context of various eukaryotic and prokaryotic expression systems and in the Examples section which follows.

Thus, the nucleic acid construct of this aspect of the present invention is capable of expressing in a host cell, a recombinant human single chain MHC class I polypeptide which includes the functional human β-2 microglobulin and the functional human MHC class I heavy chain and a linker peptide interposed therebetween. Preferably, the expressible recombinant polypeptide is as set forth in SEQ ID NO:5.

According to another preferred embodiment of the present invention, the nucleic acid construct also includes a second nucleic acid sequence encoding an antigenic peptide. The antigenic peptide is selected such that it is capable of binding a human MHC class I complex. As is further described in the Examples section which follows, various CTL specific antigenic peptides can be encoded by the second nucleic acid sequence, including but not limited to cancer cell derived antigenic peptides, virally derived antigenic peptides and the like.

Preferably the second nucleic acid sequence is translationally fused upstream of the first nucleic acid sequence, such that the nucleic acid construct according to this aspect of the present invention encodes a single chimeric amino acid sequence (chimeric polypeptide) which includes the antigenic peptide fused upstream of the functional human β-2 microglobulin which is in turn fused upstream of the functional human MHC class I heavy chain. The antigenic peptide can be fused directly to the functional human β-2 microglobulin or it can be fused thereto through a linker peptide in a manner similar to that described hereinabove with respect to the β-2 microglobulin-MHC class I heavy chain fusion.

It will be appreciated that the above described configuration of the nucleic acid construct of this aspect of the present invention is particularly advantageous since, a single construct enables the expression of a single chimeric polypeptide which includes all three components necessary for presenting specific antigenic peptides restricted to specific CTL clones, thus substantially simplifying the expression/purification and folding process.

In addition, the nucleic acid construct described above ensures that the expression product always includes a correct ratio of components of the chimeric polypeptide (1:1:1), thus traversing limitations resultant from separately expressing each component.

Alternatively, the nucleic acid construct includes a second cis acting regulatory sequence which serves for expressing the second nucleic acid sequence when introduced into a host cell.

It will be appreciated that a single cis acting regulatory sequence can be utilized by the nucleic acid construct to direct transcription of a single transcript which includes the first and second nucleic acid sequence. In such a case, an internal ribosome entry site (IRES) can be utilized so as to allow translation of the internally positioned nucleic acid sequence.

Although co-expression of the scMHC class I polypeptide and the antigenic peptide from a single nucleic acid construct is advantageous when transforming a host cell, the two nucleic acid sequences can alternatively be included in two separate nucleic acid construct which can be utilized to co-transform a single cell.

In any case, it will be appreciated that the nucleic acid construct or constructs must be configured such that the levels of expression of both the scMHC class I polypeptide and the binding peptide thereof are stoichiometrically correct (a 1:1 peptide to scMHC class I polypeptide ratio is preferred) so as to allow efficient assembly of the scMHC class I-peptide complex.

Preferably the promoter utilized by the nucleic acid construct(s) of the present invention is a strong constitutive promoter such that high levels of expression are attained for the first and second nucleic acid sequences following host cell transformation.

It will be appreciated that high levels of expression can also be effected by transforming the host cell with a high copy number of the nucleic acid construct, or by utilizing cis acting sequences which stabilize the resultant transcript and as such decrease the degradation or "turn-over" of such a transcript.

According to another aspect of the present invention there is provided a transformed host cell including the nucleic acid construct or constructs described above.

As used herein, the phrase "transformed cell" describes a cell into which an exogenous nucleic acid sequence is introduced to thereby stably or transiently genetically alter the host cell. It may occur under natural or artificial conditions using various methods well known in the art some of which are described in detail hereinbelow in context with specific examples of host cells.

The transformed host cell can be a eukaryotic cell, such as, for example, a mammalian cell, an insect cell, a plant cell, a yeast cell and a protozoa cell, or alternatively, the cell can be a bacterial cell.

When utilized for eukaryotic host cell expression, the nucleic acid construct(s) according to the present invention can be a shuttle vector, which can propagate both in *E. coli* (wherein the construct comprises an appropriate selectable marker and origin of replication) and be compatible for expression in eukaryotic host cells. The nucleic acid construct(s) according to the present invention can be, for example, a plasmid, a bacmid, a phagemid, a cosmid, a phage, a virus or an artificial chromosome.

According to another preferred embodiment of the present invention the host cell is a mammalian cell of, for example, a mammalian cell culture. Suitable mammalian expression systems include, but are not limited to, pcDNA3, pcDNA3.1 (+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

Insect cell cultures can also be utilized to express the nucleic acid sequences of the present invention. Suitable insect expression systems include, but are not limited to the baculovirus expression system and its derivatives which are commercially available from numerous suppliers such as Invitrogen (maxBac™), Clontech (BacPak™), or Gibco (Bac-to-BaC™).

Expression of the nucleic acid sequences of the present invention can also be effected in plants cells. As used herein, the phrase "plant cell" can refer to plant protoplasts, cells of a plant tissue culture, cells of plant derived tissues or cells of whole plants.

There are various methods of introducing nucleic acid constructs into plant cells. Such methods rely on either stable integration of the nucleic acid construct or a portion thereof into the genome of the plant cell, or on transient expression of the nucleic acid construct in which case these sequences are not stabily integrated into the genome of the plant cell.

There are two principle methods of effecting stable genomic integration of exogenous nucleic acid sequences such as those included within the nucleic acid construct of the present invention into plant cell genomes: p1 (i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Amtzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure, see for example, Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of stably transformed dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues. Direct DNA transfer can also be utilized to transiently transform plant cells.

In any case suitable plant promoters which can be utilized for plant cell expression of the first and second nucleic acid sequences, include, but are not limited to CaMV 35S promoter, ubiquitin promoter, and other strong promoters which can express the nucleic acid sequences in a constitutive or tissue specific manner.

Plant viruses can also be used as transformation vectors. Viruses that have been shown to be useful for the transformation of plant cell hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al, Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the nucleic acid sequences described above. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

Yeast cells can also be utilized as host cells by the present invention. Numerous examples of yeast expression vectors suitable for expression of the nucleic acid sequences of the present invention in yeast are known in the art. Such vectors are usually introduced in a yeast host cell via chemical or electroporation transformation methods well known in the art. Commercially available systems include, for example, the pYES™ (Invitrogen) or the YEX™ (Clontech) expression systems.

It will be appreciated that when expressed in eukaryotic expression systems such as those described above, the nucleic acid construct preferably includes a signal peptide encoding sequence such that the polypeptides produced from the first and second nucleic acid sequences are directed via the attached signal peptide into secretion pathways. For example, in mammalian, insect and yeast host cells, the expressed polypeptides can be secreted to the growth medium, while in plant expression systems the polypeptides can be secreted into the apoplast, or directed into a subcellular organelle.

According to a presently preferred embodiment of the present invention, the host cell is a bacterial cell, such as for example, E. coli. A bacterial host can be transformed with the nucleic acid sequence via transformation methods well known in the art, including for example, chemical transformation (e.g., $CaCl_2$) or electroporation.

Numerous examples of bacterial expression systems which can be utilized to express the nucleic acid sequences of the present invention are known in the art. Commercially available bacterial expression systems include, but are not limited to, the pET™ expression system (Novagen), pSE™ expression system (Invitrogen) or the pGEX™ expression system (Amersham).

As is further described in the Examples section which follows, bacterial expression is particularly advantageous since the expressed polypeptides form substantially pure inclusion bodies readily amenable to recovery and purification of the expressed polypeptide.

Thus, according to yet another aspect of the present invention there is provided a preparation of bacterial derived inclusion bodies which are composed of over 30 percent, preferably over 50%, more preferably over 75%, most preferably over 90% by weight of the recombinant human scMHC class I polypeptide of the present invention. The isolation of such inclusion bodies and the purification of the scMHC class I polypeptide therefrom are described in detail in the Examples section which follows.

As demonstrated in the Examples section, bacterial expression of an scMHC class I polypeptide can provide high quantities of pure and functional scMHC class I polypeptides. As such, the method of the present invention can also be applied to bacterially express mammalian scMHC class I polypeptides which to date have been expressed, with limited success, only in eukaryotic expression system.

Thus, according to another aspect of the present invention there is provided a nucleic acid construct which includes a nucleic acid sequence including a first polynucleotide encoding a functional mammalian β-2 microglobulin. The nucleic acid construct further includes a second polynucleotide encoding a functional mammalian MHC class I heavy chain which is translationally fused downstream of the first polynucleotide. The nucleic acid construct according to this aspect of the present invention further includes a cis acting regulatory sequence which is capable of directing expression of the nucleic acid sequence in bacteria. Suitable promoters and bacterial expression systems which can be utilized to express the nucleic acid sequence of this aspect of the present invention are described hereinabove.

The nucleic acid sequence according to this aspect of the present invention can be derived from, or synthesized according to, the MHC class I encoding sequences of a mammal such as, but not limited to, a mouse, a rat, a pig, and a rabbit.

It will be appreciated that the various embodiments described hereinabove for the human scMHC class I construct, which embodiments apply and are useful for the bacterial expression of the mammalian scMHC class I nucleic acid construct of this aspect of the present invention are also incorporated herein.

Thus, the present invention provides various expression constructs which can be utilized to express scMHC class I polypeptides preferably along with binding peptides thereof in eukaryotic or preferably bacterial expression systems.

According to an additional aspect of the present invention there is provided a method of producing a functional MHC class I molecule. the method according to this aspect of the present invention utilizes any of the nucleic acid constructs described for expressing, in bacteria, a single chain MHC class I polypeptide including a functional mammalian β-2 microglobulin amino acid sequence directly or indirectly covalently linked to a functional mammalian MHC class I heavy chain amino acid sequence.

Following expression, the single chain MHC class I polypeptide is isolated and purified as described below.

As is further described in the Examples section which follows, the expressed polypeptide forms substantially pure inclusion bodies which are readily isolated via fractionation techniques well known in the art and purified via for example denaturing-renaturing steps.

Preferably, the single chain MHC class I polypeptide is renatured and refolded in the presence of an antigenic peptide capable of binding the single chain MHC class I polypeptide. As is further described in the Examples section this enables to generate a substantially pure MHC class I-antigenic peptide complex which can further be purified via size exclusion chromatography.

It will be appreciated that the antigenic peptide used for refolding can be co-expressed along with the single chain MHC class I polypeptide in the bacteria. In such a case the expressed polypeptide and peptide co-form inclusion bodies which can be isolated and utilized for MHC class I-antigenic peptide complex formation.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes 1-111 Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666, 828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Peptides:

Cancer cell associated peptides G9-209-2M (IMDQVPFSV SEQ ID NO:1) and G9-280-9V (YLEPGPVTV SEQ ID NO:2), both derived from the melanoma antigen gp100 [24-26] were used for MHC binding. These peptides are modified at the MHC anchor positions 2 (in G9-209-2M) and 9 (in G9-280-9V) to improve the binding affinity to HLA-A2 [26]. The TAX 11-19 HTLV-1 peptide (LLFGYPVYV, SEQ ID NO:3) was used as a control [53].

Peptides were synthesized by standard fluorenylmethoxycarbonyl chemistry and purified to >95% by reverse phase HPLC. Following purification these peptides were used in the refolding of the single-chain MHC (scMHC)-peptide complexes and formation of scMHC-peptide tetramers further described hereinunder.

Plasmid Constructs:

A cDNA construct (SEQ ID NO:4) encoding a single-chain (sc) MHC polypeptide (SEQ ID NO:5) which includes the first three extracellular domains of HLA-A2 (HLA-A*0201, amino acids 1-275 SEQ ID NO:6) and the human $\beta$2-microglobulin polypeptide (SEQ ID NO:7) was assembled from $\alpha$1-3 and $\beta$-2 microglobulin cDNAs derived from the human T-B cell hybrid T2 cell line [27]. The human $\beta$-2 microglobulin was PCR amplified using b2M-5, 5'-AGGAGATATA CATATGATCCAGCGTACTCCAAAGAT-3' (SEQ ID NO:8) and b2M-3, 5'-CGGGCTTTGTTAGCAGCC GAATTCATTACA TGTCTCGATCCCACTTAAC-3' (SEQ ID NO:9) and linked via a 15 residue flexible linker (Gly-Ser4)$_3$ (SEQ ID NO: 10) to the N-terminus of the HLA-A2 heavy chain which was PCR amplified using A2-5, 5'-GGAGATATA CATATGGGCTCTCACTCCATGAGGTA-3' (SEQ ID NO:11) and A2-3, 5'-CGGGCTTTGTTAGCAGCC GAATTCATTAGGT GAGGGGCTTGGGCAA-3' (SEQ ID NO:12) primers. The cDNAs of both chains were used in a two-step PCR overlap extension reaction in which the 3'-end of the $\beta$-2 microglobulin was connected to the 5'-end of the HLA-A2 gene.

To perform the two-step PCR overlap extension reaction, two thirds of the linker sequence were introduced into the $\beta$-2 microglobulin sequence using PCR primers b2M-L5, 5'-GGAAGGCG TTGGCG CATATGATCCAGCGTACTCCAAAGATT-3' (SEQ ID NO:13) and b2M-L3, 5'-GGAAGCGGCGGTGGAGGCT CTGGTGGAGGTGGCAGCGGCTCTCACTCCATGA-3' (SEQ ID NO:14) while PCR primers A2-L5, 5'-GGAAGCG-GCGGTGGAGG CTCTGGTGGAGGTGGCAGCG-GCTCTCACTCCATGA-3' (SEQ ID NO:15) and A2-L3, 5'-GGGAGAATTCTTACTCCCATCTCA GGGT-GAGGGGCTTGGGCAA-3' (SEQ ID NO:16) were utilized for HLA-A2.

Following amplification, the $\beta$-2 microglobulin and HLA-A2 PCR products were combined in a 1:1 ratio and the reaction was PCR amplified using the b2M-L5 and A2-L3 primers. the PCR product was purified and subcloned into the pET-based expression vector.

The HLA-A2 and $\beta$-2 microglobulin coding sequences described above were also separately cloned in pET21 for independent expression.

The scMHC-BirA coding sequence included a peptide sequence for site specific biotinylation (LGGIFEAM KMELRD, SEQ ID NO:17), the lysine residue biotinylated underlined) linked to HLA-A2 N-terminus via a short linker (QSTRGGASGGG, SEQ ID NO:18).

The scMHC-BirA coding sequence was PCR amplified using B2M-BirA-3, 5'-CAGTAA AAGCTTTTTATCAGCCTCCGAACTGTG GATGCCTC-CACGCCGAACCTCCACCAGAACCACCTCCGGACCC GCCACCTCCCTCCCATCTCAGGGT-3' (SEQ ID NO:19) and the b2M-L5 primer described above. The resultant PCR product which included the BirA recognition sequence (SEQ ID NO:20) was purified digested and subcloned into a bacterial expression vector as shown in FIG. 1.

Expression, Refolding and Purification of scMHC-peptide Complexes:

The HLA-A2, $\beta$-2 microglobulin, and the scMHC constructs subcloned into pET21 were expressed under IPTG induction, forming intracellular inclusion bodies in BL-21 DE3 cells. Inclusion bodies were isolated and purified from the induced BL21 cells and solubilized in 6M Guanidine HCl pH 7.4. Following reduction with 65 mM DTE, inclusion bodies were refolded in a redox-shuffling buffer system (0.1M Tris, 0.5M Arginine, 0.09 mM oxidized glutathione, pH 8.0) in the presence of a 5 to 10 molar excess of the antigenic peptides derived from gp100 or the HTLV-1 viral peptide described above [26, 52]. Following refolding, the protein was dialyzed and concentrated by a Minisette system (Filtron, Northborough, Mass.) using a 10K cutoff cassette. Soluble scMHC-peptide complexes were purified by size-exclusion chromatography on TSK3000 column (TOSO-HAAS, Montgomeryville, Pa.) using PBS as an elution buffer.

Biotinylation of Recombinant scMHC-peptide Complexes and Tetrameric scMHC-peptide Complexes:

The s.c-b2-A2-BirA (scMHC-BirA) construct also expressed as described above was refolded in the presence of peptides 209 or 280 and purified by size exclusion chromatography on TSK3000 column (elution buffer 10 mM Tris-HCl pH 8). The scMHC-peptide-BirA complexes were concentrated to 20-30 mM (1-1.5 mg/ml) by Centricon 30 (Amicon) and were then subjected to enzymatic biotinylation for 16 hr at 25° C. using a biotin protein ligase-Bir A enzyme (AVIDITY). Buffer exchange and removal of excess biotin from the biotinylated complexes was performed using Centricon 30 ultrafiltration. Tetrameric arrays of biotinylated scMHC-peptide complexes were formed by the addition of streptavidin (Sigma, St. Louis, Mo.) at a molar ration of 4:1 scMHC-peptide complex:streptavidin, respectively.

ELISA Assays:

Maxisorb immunoplates (Nalge Nunc, Naperville, Ill.) were coated overnight at 4° C. with 1 mg/ml anti-HLA monoclonal antibody BB7.2 (ATCC HB82) and blocked using PBS including 3% BSA. Biotinylated anti-HLA W6/32 monoclonal antibody (ATCC HB95) was used for detection of the HLA complex via a streptavidin-peroxidase conjugate.

In addition, biotinylated or unbiotinylated scMHC-BirA-peptide complexes were incubated for 30 minutes at room temperature with washed MagnaBind™ streptavidin beads (PIERCE). An external magnetic field was used to separate biotinylated complexes bound to the beads from unbound material. The supernatant was pooled away from bound sample and the beads were blocked with 2% MPBS (PBS +2% semi-skimmed milk powder) for 30 minutes at room temperature. The biotinylated complexes were subsequently assayed with the conformational dependent antibody W6/32 and detected using anti-mouse IgG-peroxidase.

Circular Dichroism Spectra:

The circular dichroism spectra of the scMHC-peptide complexes was measured at room temperature via a spectropolarimeter (JASCO 500) adjusted to a sensitivity of 0.5 mdeg/cm and a scan speed of 10 nm/minute. Scans were performed between 195 and 275 nm at a protein concentration of 0.27 mg/ml. Secondary structure calculations were measured using published programs [29].

Mass Spectrometry Analysis of scMHC-peptide Complexes:

The scMHC-peptide complex was resolved by HPLC on a 2.1×30 mm C-8 column (AQUAPORE RP-300, Applied Biosystems), and eluted with a linear gradient of 15-65% Acetonitrile (ACN) in 0.05 TFA, at 1.25%/min and a flow rate of 150 ml/min. The sample was microsprayed directly from the HPLC column into an electrospray (ESI) ion trap mass spectrometer (LCQ, Finnigan) and analyzed in the positive ion mode. The mass estimation of the proteins was done using the deconvolution algorithm, which transforms an ESI mass spectral plot of relative abundance versus mass-to-charge ratios into a plot of relative abundance versus mass. Each sequence of multiply charged ion peaks in the acquired mass spectrum corresponding to one sample component, is converted into a single peak positioned at the molecular mass M in the deconvoluted spectrum.

CTL Clones and CTL Stimulation Assays:

CTL clones specific for melanoma peptides were provided by Drs. Steven Rosenberg and Mark Dudley (Surgery Branch, National Cancer Institute, NIH). These CTL clones were generated by cloning from bulk cultures of PBMCs acquired from patients receiving peptide immunizations [24]. The CTLs were subsequently expanded using irradiated PBMCs and the OKT3 antibody (30 ng/ml) in the presence of 50 CU/ml IL-2.

The CTL clones ($1 \times 10^5$/well) were washed in tissue culture medium and incubated in duplicates or triplicates with various concentrations of scMHC-peptide tetramers in tissue culture medium for 24 hrs at 37° C. Alternatively scMHC-peptide complexes were immobilized onto Maxisorb immunoplates over night at 4° C. and CTL clones in culture medium were subsequently added to the wells and incubated for 24 hrs at 37° C. Following incubation supernatants were collected via centrifugation and IL-2 and IFNg present in the culture supernatants were assayed using a double sandwich antibody-capture enzyme immunoassay (Flexia, BIOSOURCE, Camarillo, Calif.). Concentrations of IL-2 and INFγ in the culture supernatants was determined against a calibration curve of recombinant human IL-2 and INFγ.

Experimental Results

Expression, Refolding, and Purification of Recombinant Single-chain MHC-peptide Complexes:

To produce soluble single-chain MHC-peptide complexes we subcloned the genes encoding the single-chain MHC into a pET system expression vector in which expression is driven by the phage T7 promoter.

The plasmid constructs used in this study are described in FIG. 1. Expression of the scMHC gene in *E. Coli* BL21 cells was very efficient and recombinant protein accumulated as insoluble intracellular inclusion bodies. The single-chain MHC could be detected as the major band on SDS-PAGE of solubilized whole cells (not shown) as well as isolated purified inclusion bodies (FIG. 2a). The expression of the scMHC protein was comparable to that of the separate components, i.e., the transmembrane HLA-A2 heavy chain and β-2 microglobulin (FIG. 2a). Very efficient expression was also obtained for the scMHC-BirA protein (FIG. 2b). Purified inclusion bodies contained 80-90% recombinant scMHC. Inclusion bodies were purified, solubilized in 6M guanidine HCl, and refolded by in vitro redox-shuffling buffer system in the presence of the antigenic peptide. Three different peptides were used for the refolding of the scMHC molecules. Two peptides (G9-209-2M and G9-280-2V) are tumor associated antigens derived from the melanoma common antigen gp100 [26] and one is a viral peptide derived from HTLV-1 (TAX) [53]. These peptides were previously shown to be HLA-A2 restricted [26, 53].

Refolded complexes were dialyzed and concentrated following by purification using size-exclusion chromatography on TSK3000 column. SDS-PAGE analysis, under non-reducing conditions, of refolded purified scMHC-peptide complexes revealed a homogenous monomeric population of molecules that migrated as a uniform single band corresponding to the scMHC molecule with an apparent molecular weight of 45 kDa as calculated according to the relative migration against a set of molecular weight markers (FIGS. 3a-b). As shown in FIGS. 3a-b, purified homogenous scMHC-peptide complexes were obtained with all three peptides tested. When the scMHC was refolded in the absence of a peptide, a highly aggregated protein was observed which was composed of a heterogeneous population of molecules as analyzed by size-exclusion chromatography and SDS-PAGE; this indicates the existence of an unstable population of molecules that are improperly folded (data not shown). Thus, a uniform population of monomers could only be found in the peptide-induced refolding preparations. The refolded scMHC-peptide complexes could be stored at −70° C. and re-used upon thawing. The yield of the refolded purified single-chain MHC complexes was 20-25%, i.e. 20-25 mg of a purified soluble complex was obtained from 100 mg of refolded inclusion body protein.

Similar results were obtained with the scMHC-BirA-peptide complexes, which contain a sequence tag at the C-terminus of the HLA-A2 for site specific biotinylation (FIG. 3c). The apparent molecular weight of 48 kDa was observed for this molecule reflecting the increase in the size of the scMHC molecule predicted by the addition of the BirA peptide tag and the linker connecting it to HLA-A2.

Thus, these results indicate that scMHC-peptide complexes can be produced in vitro by refolding of E. Coli inclusion bodies in the presence of antigenic peptides. The refolding process is efficient and a homogenous population of complexes can be obtained with high yields and purity.

Biochemical and Biophysical Characterization of Single-chain MHC-peptide Complexes:

As shown in FIGS. 3a-c, the scMHC peptide complexes were pure and homogenous as judged by SDS-PAGE. Size exclusion chromatography on TSK3000 column revealed that the purified scMHC-peptide complexes were eluted as monomers with a molecular mass of 45 kDa (not shown). When purified complex was concentrated by ultrafiltration to 0.15 mM (~6 mg/ml) and analyzed for its molecular form on a size-exclusion TSK3000 column in PBS, no indication of dimerization or aggregation, was observed.

Figure 4:
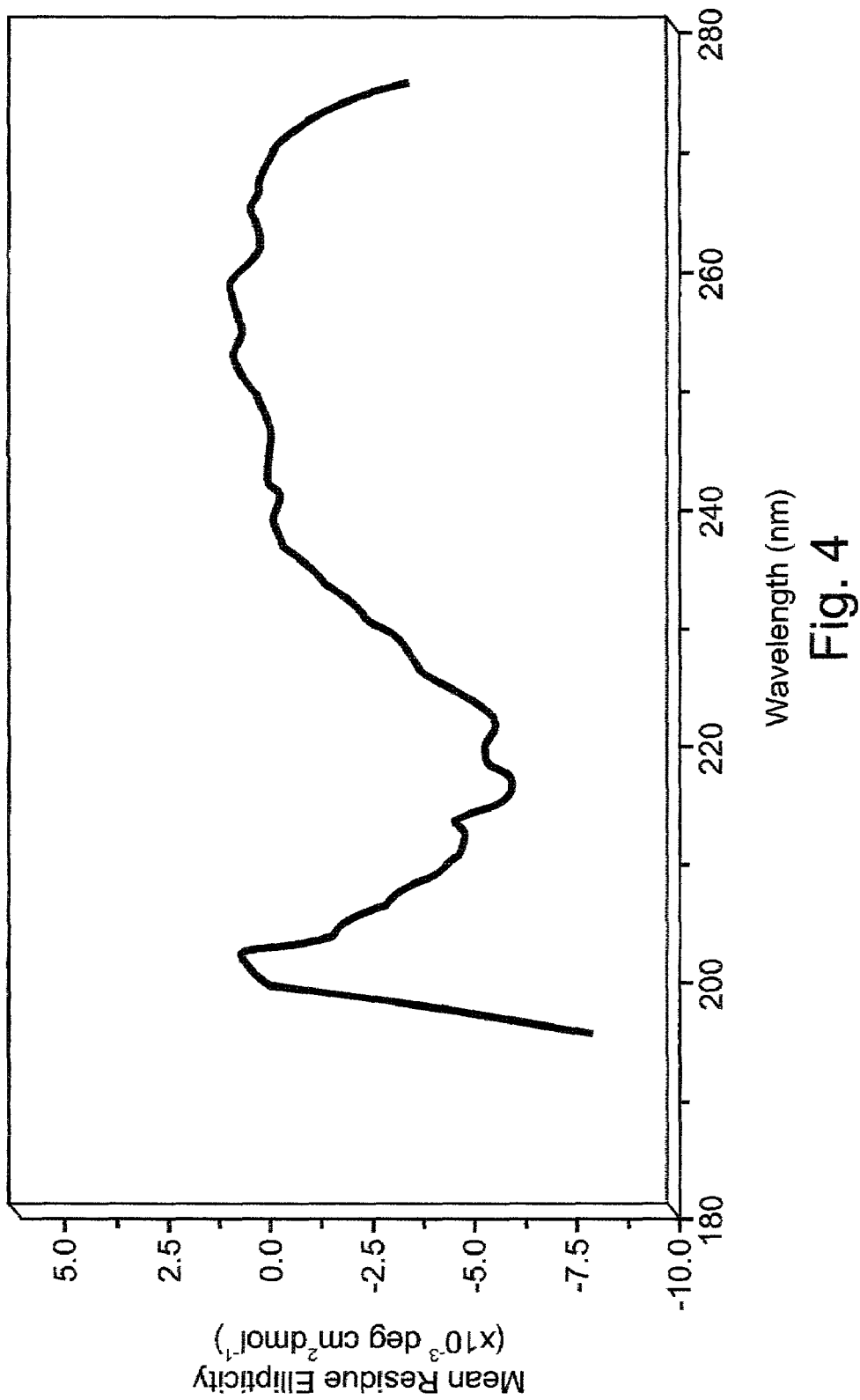
FIG. 4 is a CD spectra analysis of a refolded single-chain MHC-peptide complex collected and analyzed as described in the Examples section below.

To evaluate the secondary structure of the single-chain MHC-peptide complex, protein purified through size-exclusion chromatography was examined by circular dichroism (CD) spectroscopy (FIG. 4). Spectra of the complex showed a characteristic minima at 218 nm consistent with a largely β-sheet structure. When analyzed for secondary structural calculations the spectra was indicative of a specific pattern of secondary structure which included 62% β-sheet, 5% β-turn, 8% α-helix and 18% aromatic side chain contribution. When denatured at 80° C., the spectra profile indicated that most of the characteristic β-sheet structure was lost and the CD signal increased, indicating random coils were generated as the result of denaturation. The melting curve showed that the complex containing peptide G9-209-2M was thermally stable with a melting temperature of approximately 60° C. (data not shown). These results are similar to the thermal denaturation curves for HLA-A2 complexed with influenza virus peptides as was monitored by the change in the CD signal at 218 nm [31]. Thus it is concluded that these secondary structure features are characteristic of correct folded MHC-peptide complexes [31].

Figure 5A:
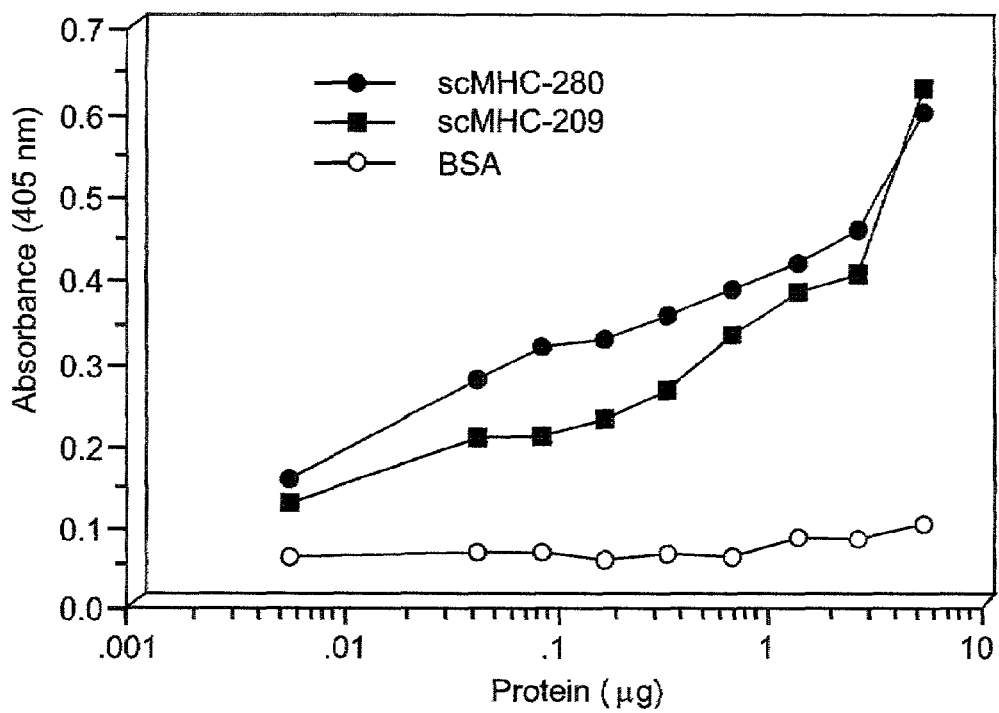
FIGS. 5a-b are graphs depicting antibody analysis of single-chain MHC-peptide complexes. Binding of conformation-specific antibodies to refolded and purified scMHC-peptide complexes was performed by a capture double sandwich ELISA assay as further described in the Examples section. Anti-HLA-A2 specific mAb BB7.2 antibody was used to capture the soluble scMHC-peptide complex and the biotinylated mAb W6/32 specific for fully assembled, peptide-containing HLA-A2 was used for detection (FIG. 5a). The reaction was developed using streptavidin-peroxidase conjugate. Specific recognition of the single-chain MHC-BirA-peptide complex by the W6/32 antibody was also determined for biotinylated or unbiotinylated complexes that were immobilized to streptavidin-coated magnetic beads (FIG. 5b).

The refolded scMHC-peptide complexes were also assayed using conformation-specific antibodies, which recognize MHC-peptide complexes only when correctly folded. As shown in FIG. 5a, the anti-HLA-A2 specific mAb fragment BB7.2 and the mAb fragment W6/32 specific for a fully assembled, peptide-containing HLA-A2 detected soluble scMHC-peptide complex. The W6/32 antibody specifically recognized, in a concentration dependent manner, the refolded and purified scMHC complexes containing any of the two gp100-derived peptides indicating that the complexes are correctly folded, include the peptide, and are structurally functional.

Figure 5B:
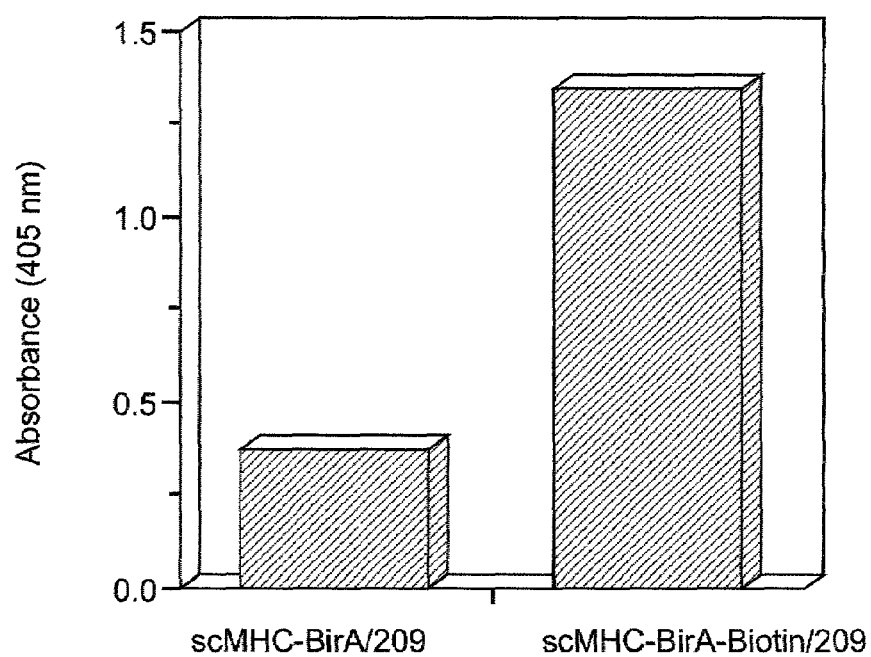

The specific recognition of the scMHC-BirA-peptide complex by the W6/32 antibody was also effected when tested on biotinylated complexes that were immobilized to streptavidin-coated magnetic beads (FIG. 5b). The ELISA signal from beads coated with biotinylated scMHC-BirA-peptide complexes was 5-6 fold higher than scMHC-BirA-peptide complex that was not subjected to biotinylation by the BirA enzyme (FIG. 5b).

Figure 6A:
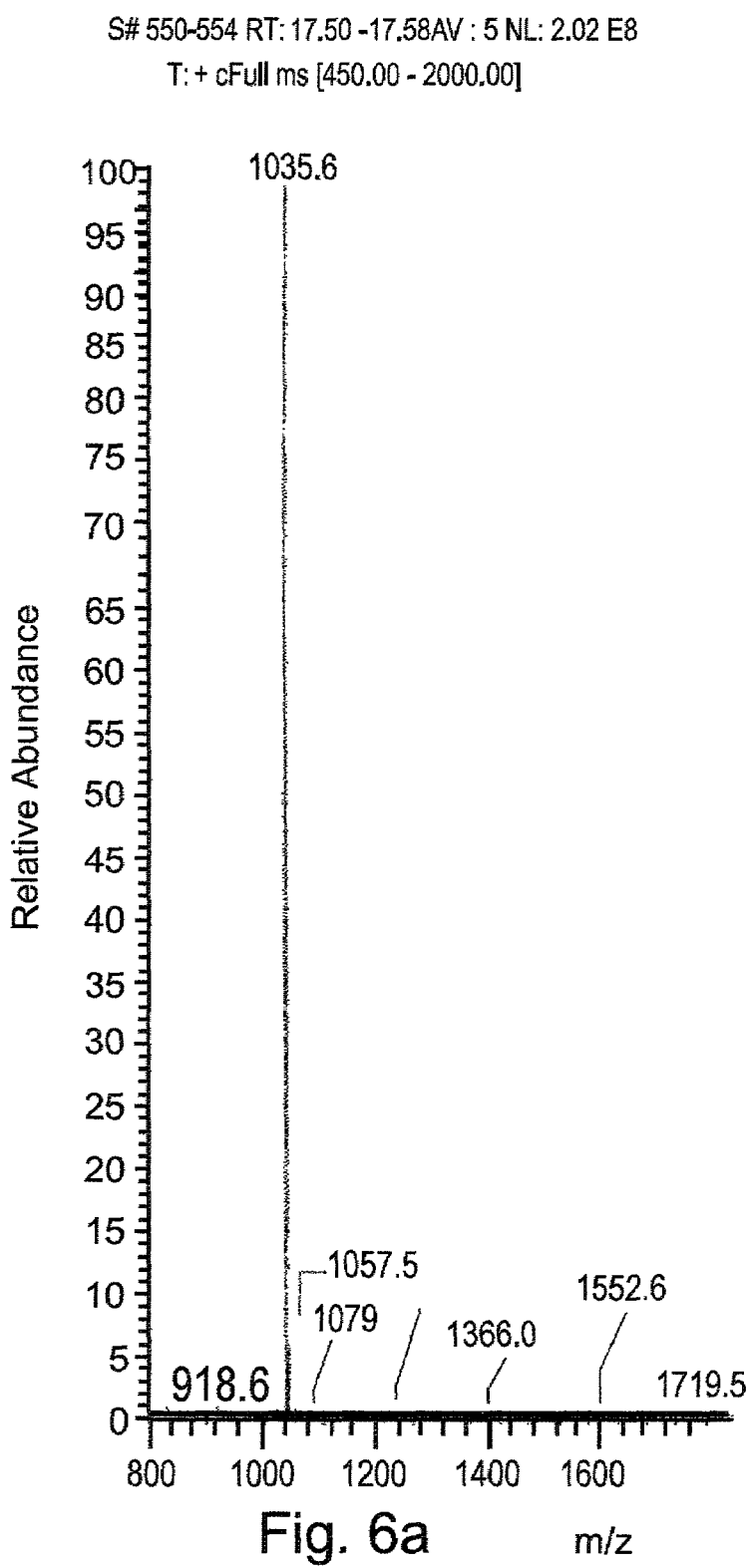
FIGS. 6a-c depict mass spectroscopy analysis of single-chain MHC-peptide complexes. The scMHC-209 complex was resolved by HPLC on a C-8 hydrophobic column, and eluted with a linear gradient of acetonitrile in TFA, The sample was microsprayed directly from the HPLC column into an electrospray ion trap (ESI) mass spectrometer (LCQ) and analyzed in the positive ion mode.

Mass spectrometry analysis was performed in order to clearly demonstrate that the scMHC complex is folded correctly and includes the peptide. The refolded and purified complex was concentrated to 6 mg/ml and a sample was subjected to analysis by electron spray mass spectrometry. The complex sample was first resolved by HPLC on a C-8 column and was subsequently eluted with a linear gradient of Acetonitrile in TFA, leading to separate sequential elution of the peptide and the scMHC protein from the column. The eluted samples were microsprayed directly from the HPLC column into an electrospray ion trap (ESI) mass spectrometer and analyzed in the positive ion mode. As shown in FIG. 6a, the eluted peptide has an expected mass of 1035 dalton which corresponds to the mass of the G9-209-2M peptide used for refolding the scMHC-peptide complex. This was the only peptide detected indicating that the refolded complex is a homogenous population of molecules containing a single specific peptide. A minor peak with a mass of 1057 daltons was also observed, which peak corresponds to the G9-209-2M peptide including a sodium ion which probably originated from the PBS buffer in which the complex was purified and concentrated prior to analysis.

Figure 6B:
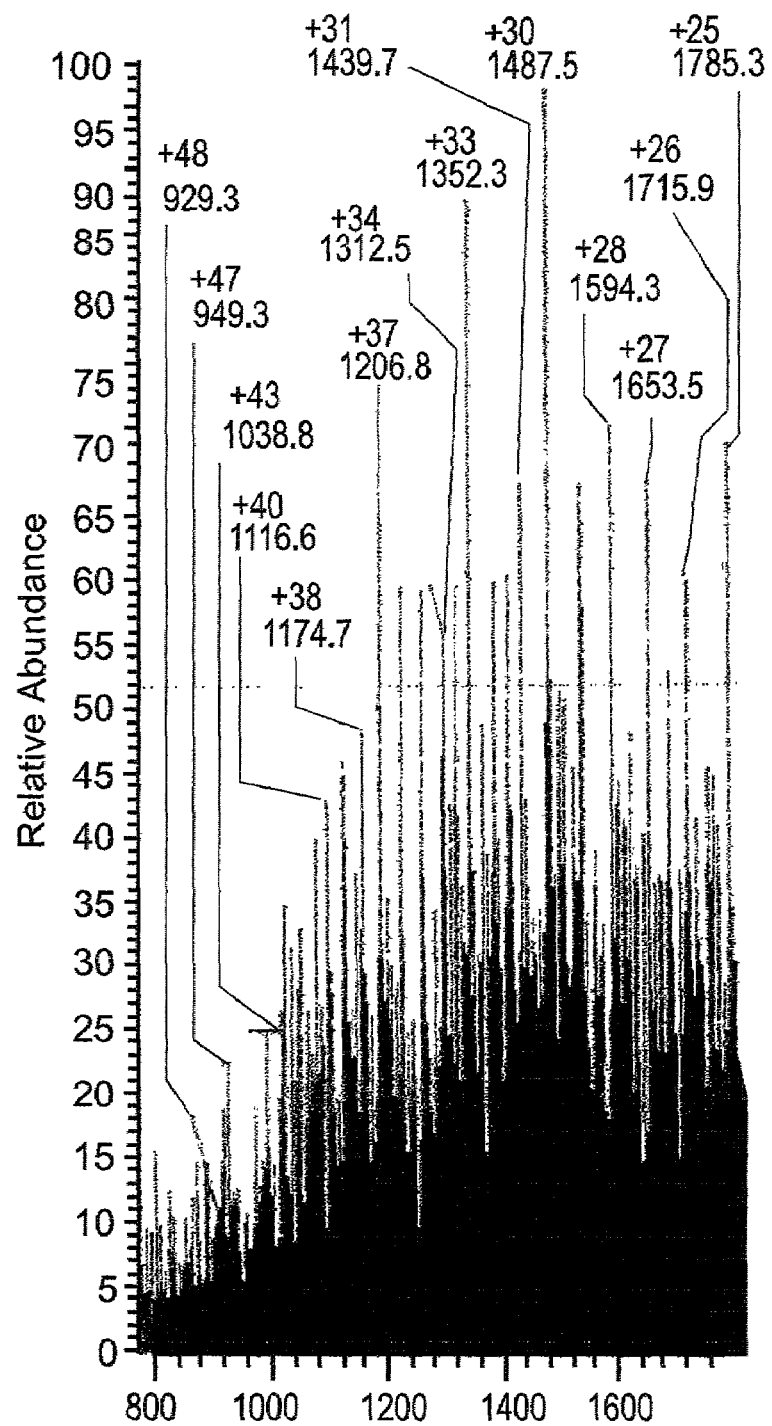
Figure 6C:
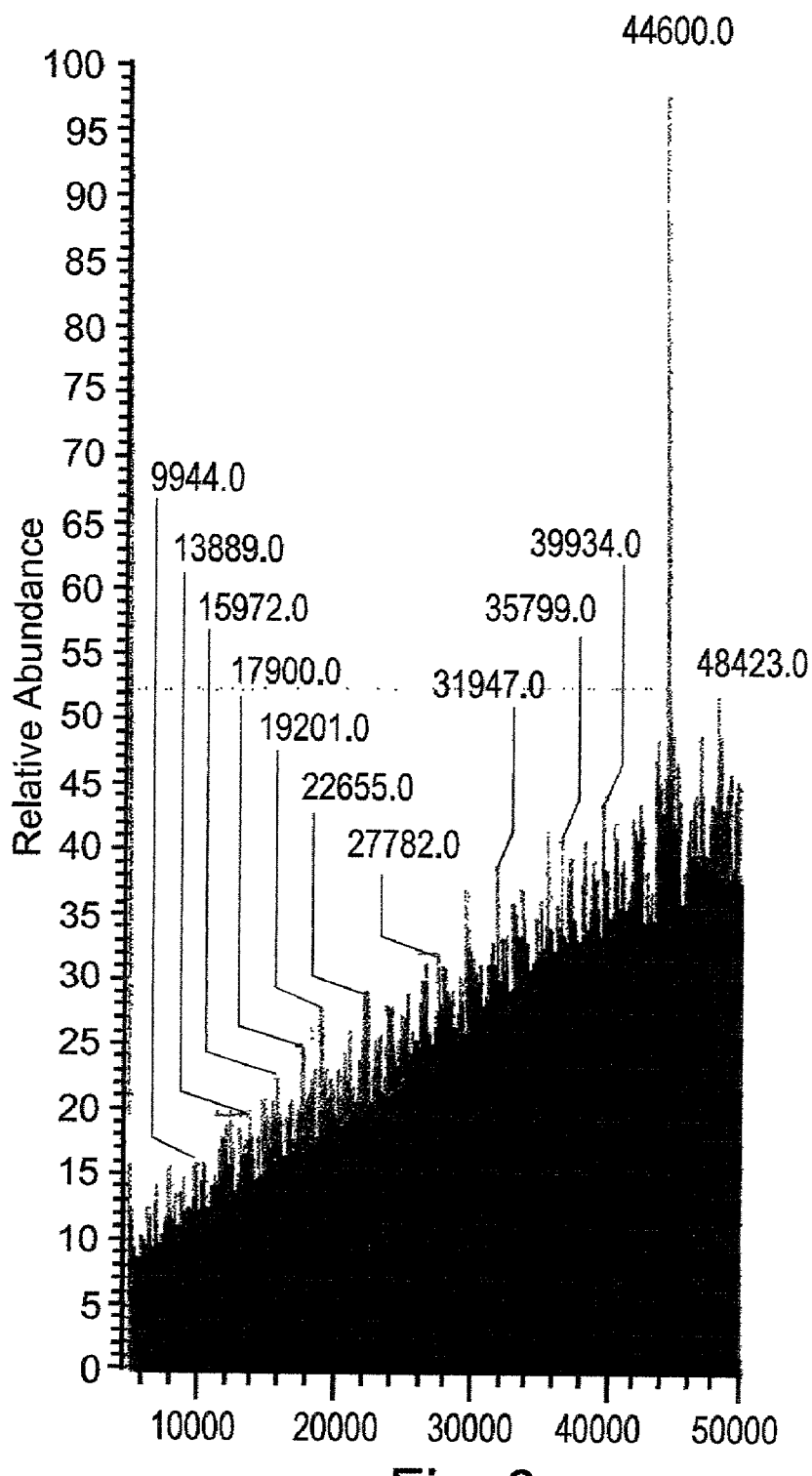

The mass estimation of the scMHC complex was done using a deconvolution algorithm, which transforms an ESI mass spectral plot of relative abundance versus mass-to-charge ratios into a plot of relative abundance versus mass (FIGS. 6b-c). Each sequence of multiply charged ion peaks in the acquired mass spectrum (FIG. 6b) which corresponds to one sample component, is converted into a single peak positioned at the molecular mass (M) in the deconvoluted spectrum (FIG. 6c). As shown in FIG. 6c, the deconvoluted spectrum revealed a single peak with a mass of 44.6 kDa corresponding to the expected molecular weight of the scMHC protein. As shown above for the peptide, this was the only identified protein peak in the analyzed spectrum indicating that the protein consists of a very homogenous population of folded complexes. Stoichiometric estimation of the eluted peptide performed according to the mass spectrometry data, revealed that all refolded and purified scMHC molecules are complexed with the peptide.

Biological Activity of Single-chain MHC-peptide Complex:

A CTL stimulation assay using cloned CTLs specific for the G9-209-2M peptide was utilized to test the biological activity of the scMHC-peptide complex.

Figure 7A:
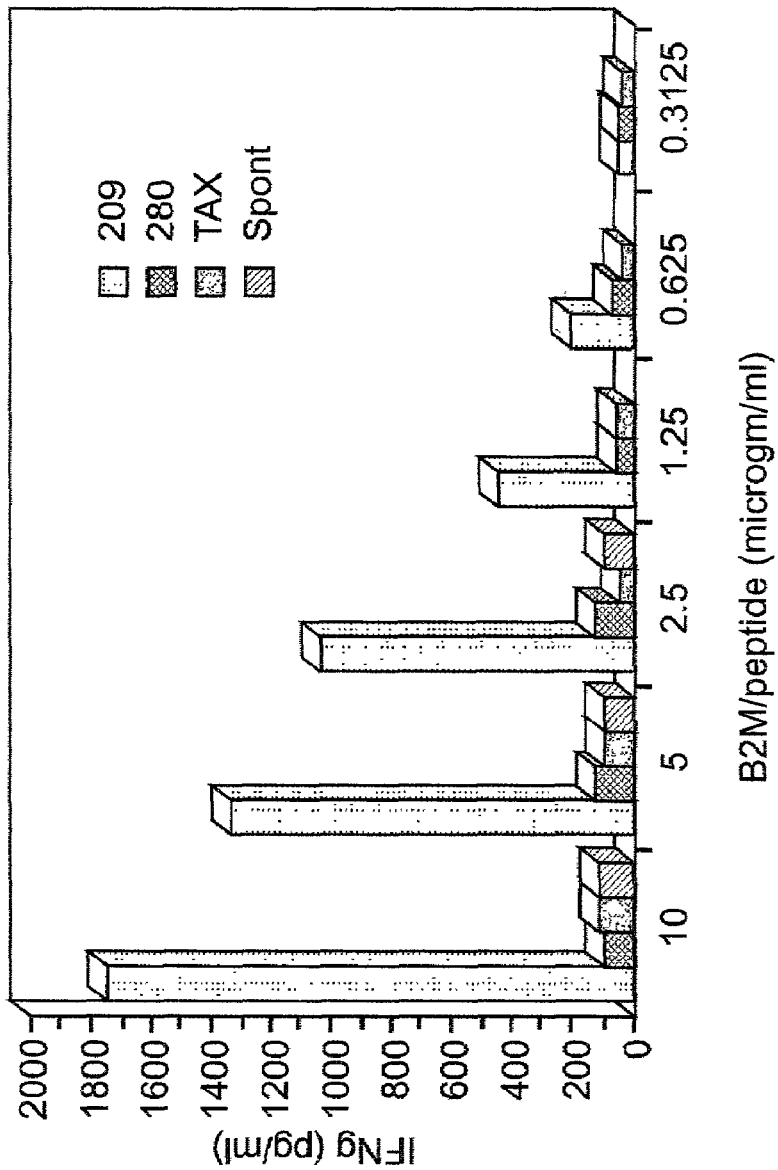
FIGS. 7a-c are graphs depicting the biological activity of single-chain MHC-peptide complexes as determined by measuring the release of IFNg from specific CTL clones.

The recombinant purified scMHC complexes that were produced with the 3 different peptides (G9-209-2M, G9-280-9V, and TAX) were immobilized on a microtiter plate and tested for the ability to induce CTL activation. As shown in FIG. 7a, the single-chain MHC molecule bound to the g9-209-2M peptide induced specific activation of the g209-specific CTL clone R6C12 as determined by interferon-g levels. On the other hand, the complexes bound to the g280 and TAX peptides did not induce specific activation.

Figure 7B:
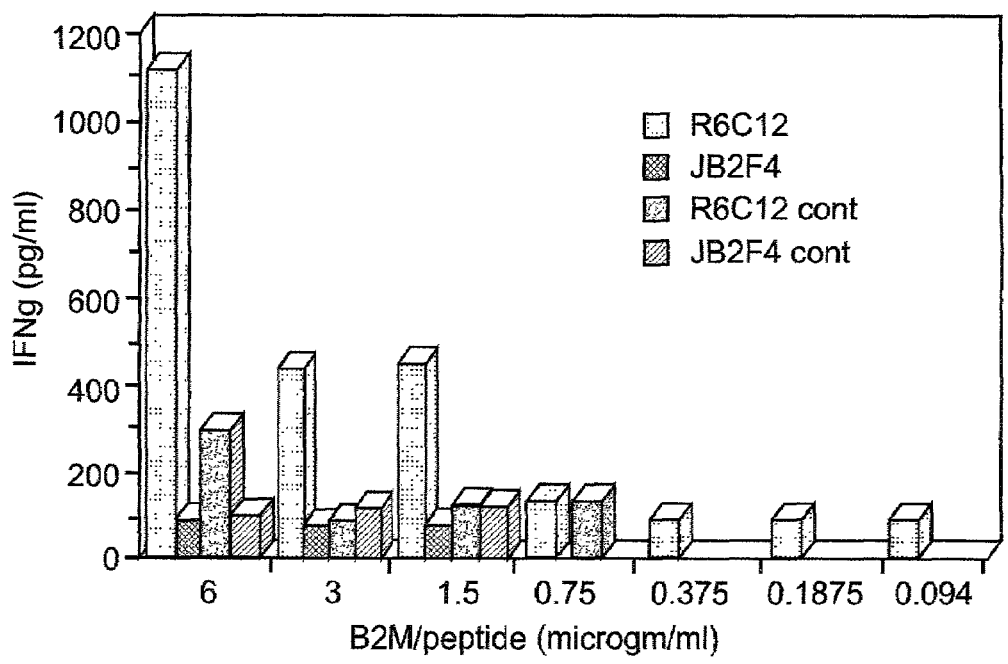
Figure 7C:
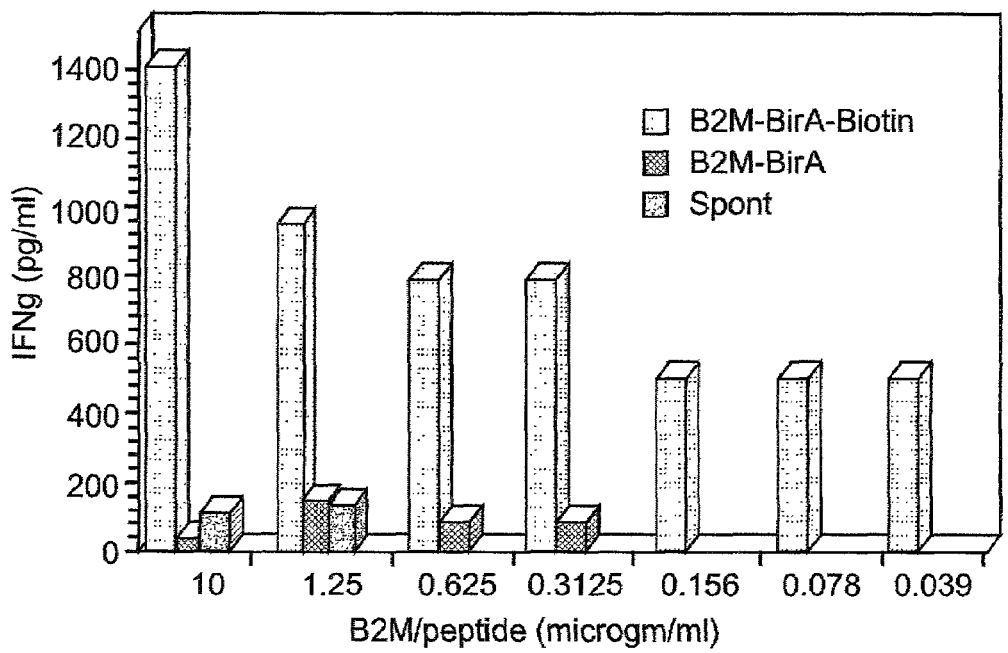

The ability of soluble scMHC-peptide complexes to induce T cell activation in solution was also tested by generating scMHC-peptide tetramers composed of the scMHC-peptide molecule containing the sequence tag for site-specific biotinylation. Refolded and purified peptide containing scMHC- BirA complexes were biotinylated using the BirA enzyme. Following purification of the scMHC-BirA complexes tetramers were formed by incubation with streptavidin. The biological activity of the scMHC-BirA-peptide tetramers was tested by their ability to activate the corresponding CTL clone. As shown in FIG. 7b, the tetramers containing the G9-209-2M peptide activated the 209-specific CTL clone R6C12 but not the Mart-1 specific CTL clone JB2F4, indicating that the refolded scMHC-peptide complexes are functional and specific. As shown in FIG. 7c, the ability of the single-chain MHC-BirA-peptide complex to activate the 209-specific CTL clone was tested with or without biotinylation of the scMHC protein and subsequent incubation with streptavidin. As is evident from this Figure, only the biotinylated MHC-BirA-peptide which can form tetrameric complexes activates the 209-specific CTL clone in solution thus T cell activation in solution requires the multimerization of MHC complexes in the form of tetramers which increase the avidity of MHC-TCR interactions.

The tetramer-induced activation of the specific G9-209-2M CTL clone was more efficient compared to the activation induced by high density coating of microtiter plates since tetramers were still able to i o induce specific CTL activation at ng/ml concentrations (FIGS. 7a and 7c).

Figure 8A:
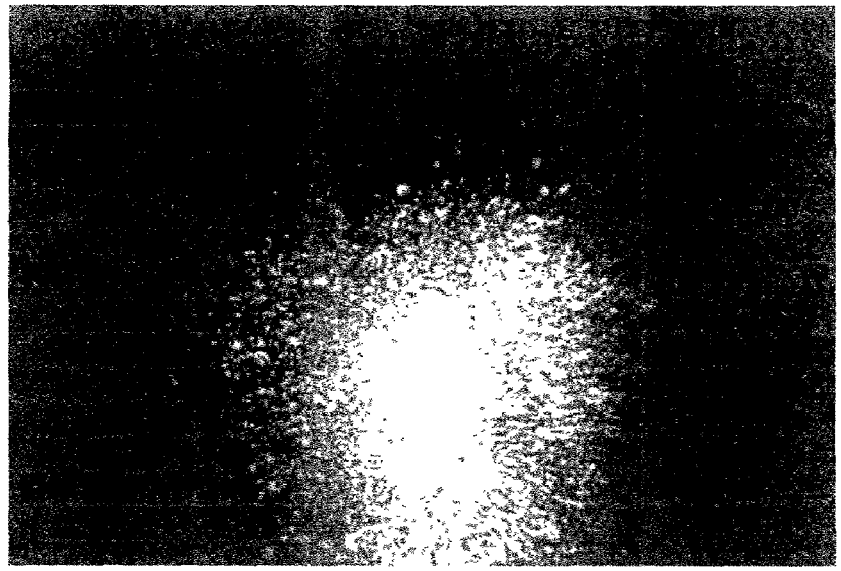
FIGS. 8a-e are microscopic images of microtiter plate wells containing the G9-209-2M-specific CTL clone R6C12 incubated with biotinylated and thus tetramer forming scMHC-BirA-209 complexes or unbiotinylated scMHC-BirA-209 complexes which are incapable of forming tetramers and which served as controls. Cell agglutination was peptide specific and dependent on the concentration of the scMHC-BirA-209 tetramer (FIG. 8b). As the concentration of tetramers increased, increased cell agglutination (rosette formation) was observed (FIGS. 8c-e). CTLs incubated with unbiotinylated scMHC-BirA-209 complexes and streptavidin did not exhibit any morphological appearance indicating of cell agglutination (FIG. 8a).
Figure 8B:
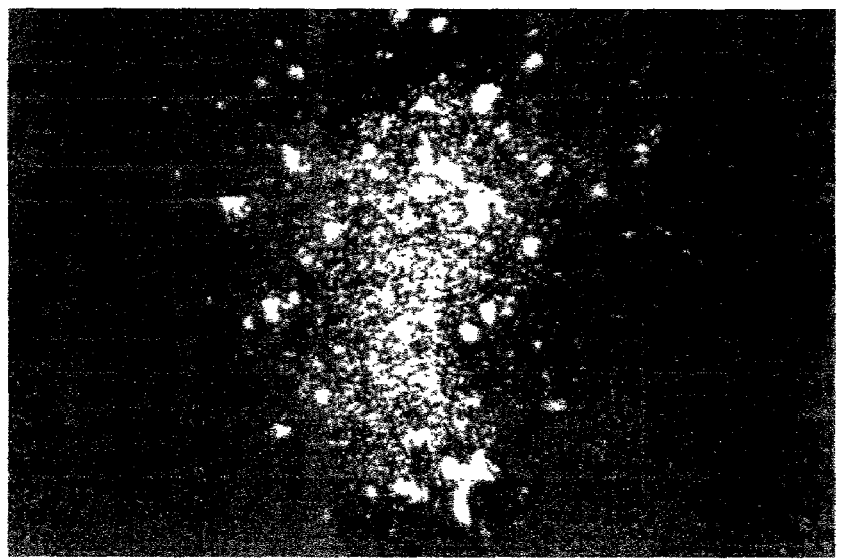
Figure 8C:
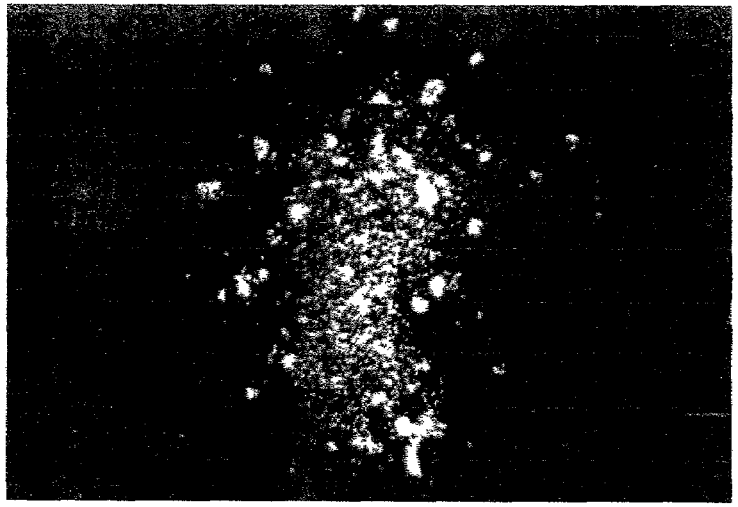
Figure 8D:
Figure 8E:
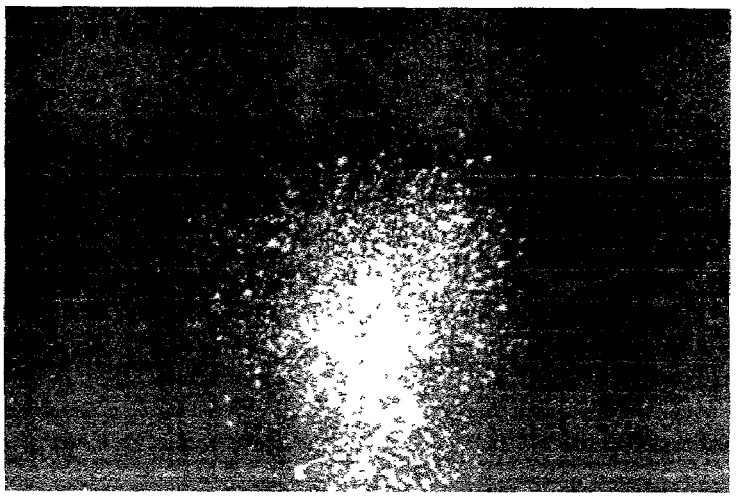

Microscopic observation of the activated CTL clone incubated with the 209-containing MHC tetramers revealed that the cells were agglutinated (FIG. 8b). This is due to the significant increase in TCR-MHC avidity and enhanced cell to cell contacts effected by multipoint binding and cross-linking which is caused by the high concentration of MHC tetramers. These morphological effects were peptide specific and dependent on the concentration of the scMHC-BirA-peptide tetramer (FIG. 8b). As the concentration of tetramers increased, increased cell agglutination (rosette formation) was observed (FIG. 8c-e).

CTLs incubated with unbiotinylated scMHC-BirA-209 complexes and streptavidin which served as a control did not exhibit any morphological appearance indicating of cell agglutination (FIG. 8a).

In addition, no agglutinations were observed when the Mart-1 specific CTL clone was incubated with the same concentrations of the g209-specific scMHC tetramer (data not shown).

The scMHC tetramers also specifically stained CTL clones which recognize the MART-1 specific peptide 27-35. As shown in FIG. 9a, the scMHC/Mart tetramers specifically recognized a specific CTL clone which was not recognized by the scMHC/TAX tetramers (FIG. 9b).

Figures 10A, 10B:
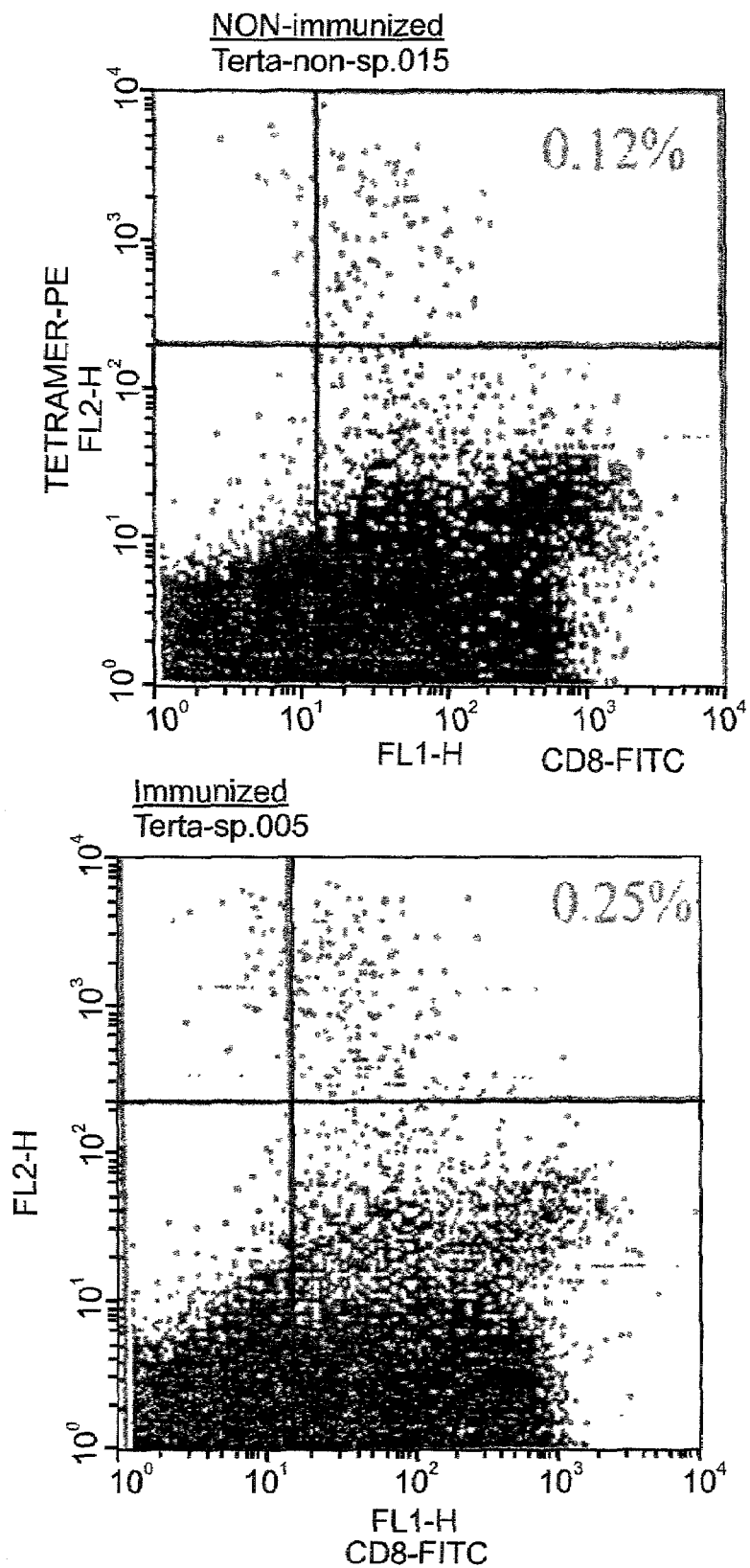
FIGS. 10a-b are FACS analysis images of a heterogeneous population of T-cells from an HLA-A2 transgenic mice immunized with the TAX peptide.

ScMHC tetramers were also used to stain a heterogeneous population of T cells from the spleen of transgenic mice (expressing HLA-A2) which were immunized with the TAX peptide. As shown in FIGS. 10a-b the number of specific high avidity CD8+ T cells increased by 2-fold when non-immunized and immunized mice were compared. Thus, as clearly demonstrated above, the scMHC tetramers generated according to the teachings of the present invention can be utilized to detect and isolate antigen-specific subpopulations of T cells.

The results presented herein suggest that the recombinant scMHC-peptide complexes generated according to the teachings of the present invention are functional, in both the monomeric and the complexed tetrameric forms.

Recombinant MHC-peptide tetramers are a very important tool for the molecular characterization of immune responses.

Fluorogenic tetramers have been widely used for the characterization of CTL responses and have afforded many advantages over previous techniques, particularly the ability to directly quantify and phenotype Ag-specific CTLs ex-vivo [32-35, 38-53].

It has also been suggested that the enhanced avidity afforded by multimerization of peptide-MHC may allow binding to TCRs with affinities too low to ever generate ligand-induced physiological responses. MHC-peptide tetramers can be utilized in the field of viral infections for direct visualization of antigen-specific CD8+ cells in HIV and EBV infection [33, 40, 41, 45, 52], animal models of viral infection [41-43] and direct analysis of viral-specific CD8+ cells in patients with human T cell lymphotropic virus-associated myelopathy [53].

MHC-peptide tetramers might also revolutionize the field of anti cancer immunity and immunotherapy since they can be used to identify low frequency anti-tumor CD8+ immune responses. This has already been demonstrated for melanoma where there is now considerable evidence that human tumors often express antigens that make them susceptible to lysis by CTLs [32, 36, 37, 48, 50]. Recently the use of tetrameric soluble class I MHC-peptide complexes for characterizing melanoma-specific CTL ex vivo has been reported [36]. An important advance in the field of immunotherapy will be the ability to use this technology for adoptive immunotherapy. The use of MHC-peptide tetramers will allow the isolation of CTLs specific for one melanoma epitope from a mixed CTL population using tetramer-driven cell sorting [36]. Polyclonal CTL lines can be utilized to efficiently lyse autologous tumor cells by generating monoclonal CTL lines against different melanoma epitopes using direct tetramer-driven CTL cloning [24, 36].

The ability to efficiently generate recombinant MHC-peptide complexes, with a large variety of antigenic peptides, all related to one disease (for example, melanoma) may lead to improved modes of immunotherapy. Thus, it will enable the simultaneous isolation and cloning of tumor-specific CTL clones specific for the various peptides ex-vivo, accompanied with specific PCR typing of tumor associated peptides expressed by individual patients. The specific clones an then be expanded for adoptive transfer according to the tumor associated antigen (peptide) expression profile of the patient.

The availability of recombinant MHC-peptide complexes is of interest not only for the generation of MHC tetramers but also for rapid, sensitive, and reliable MHC-peptide binding assay to identify high affinity MHC binding T cell epitopes. These complexes can be used also in in-vitro primary CTL induction studies to define, among the various MHC binders, those peptides that are immunogenic.

They may be used for CTL in vitro induction as well as for the generation of MHC-peptide tetramers and analysis of specific immune responses or direct selection of CTLs from heterogeneous lymphocyte populations by tetramer-driven cell sorting and analysis.

Recombinant scMHC-peptide complexes can also be used to generate specific antibodies by phage display technology [54]. Such antibodies with TCR-like specificity can be a valuable tool for studying antigen presentation by tumor cells as well as to develop novel targeting agents for immunotherapy.

To date, studies utilizing MHC complexes, some of which are described above, are limited by MHC purification methods which are incapable of producing the required amounts of soluble and functional monomeric or multimeric MHC-peptide complexes.

Thus, the expression method of the present invention provides an invaluable tool for advancing studies with MHC complexes by providing an easy and rapid method for producing large amounts of highly pure and functional monomeric or multimeric scMHC-peptide complexes without the need for arduous and time consuming purification steps such as peptide exchange employed by prior art methods. In addition, the present invention provides a novel human single chain MHC class I polypeptide which is functional in activating CTL clones when utilized as either a monomer or a multimer.

Example 2

Co-expression of the scMHC Complex and Peptide

It will be appreciated that the various scMHC constructs described above and any mammalian scMHC class polypeptides can also be co-expressed in *E. coli* or any other prokaryotic or eukaryotic expression systems along with the respective binding peptides thereof, thus negating the need for separately providing the binding peptide. Thus according to this method of the present invention, a single construct can be configured so as to express both the scMHC class I polypeptide and respective binding peptide coding sequences in the same cell by utilizing for example two separate promoters or an internal ribosome entry site. Alternatively the cells of the prokaryotic or eukaryotic expression system be co-transformed with two expression constructs each expressing a single coding sequence and each having a specific selection marker.

Suitable eukaryotic expression systems include, but are not limited to mammalian or insect cell cultures, plant protoplasts, plant cell cultures, whole plants, yeast cells or protozoan cells. It will be appreciated that when expressed in eukaryotic expression systems the produced scMHC class I polypeptide preferably includes a transit peptide (signal sequence) such that the expressed polypeptide is secreted outside the cell (into the apoplast in plant cell cultures or whole plants) so as to avoid interaction with endogenous peptides.

It will be appreciated that the construct or constructs must be configured such that the levels of expression of both the scMHC class I polypeptide and the binding peptide thereof are stoichiometrically correct.

Thus, a cell which expresses both coding sequences can produce a fully functional scMHC-peptide complex which can be purified via suitable isolation protocols well known in the art. It will be appreciated that a bacterial expression system is especially advantageous in this case since the scMHC-peptide complex expressed thereby can form substantially pure inclusion bodies when suitable expression conditions are employed. Thus, even if the scMHC-peptide complex disassembles under denaturing conditions utilized for solubilizing the inclusion bodies, suitable renaturation conditions can be used so as to reform a functional scMHC-peptide complex.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this application shall not be construed as an admission that such reference is available as prior art to the present invention.

LIST OF REFERENCES

Additional References Are Cited in the Text

1. Rammensee, H. G., Falk, K., and Rotzschke, O. 1993. Peptides naturally presented by MHC class I molecules. *Ann. Rev. Immunol.* 11: 213-244.
2. Germain, R., and Margulies, D., 1993. The biochemistry and cell biology of antigen processing and presentation. *Ann. Rev. Immunol* 11: 403-450.
3. Matsumura, M., Fremont, D. H., Peterson, P. A., and Wilson, I. A. 1992. Emerging principals for the recogntion of peptide antigens by MHC class I molecules. *Science* 257: 927-34.
4. Davis M M, Boniface J J, Reich Z, Lyons D, Hampl J, Arden B, and Chien Y. 1998. Ligand recognition by alpha beta T cell receptors. *Annu Rev Immunol* 16:523-44
5. Hansen, T. H., and Lee, D. R. 1997. Mechanism of class I assembly with beta 2 microglobulin and loading with peptide. *Adv Immunol.* 64:105-37
6. Lanzavecchia, A., G. Lezzi, and A. Viola. 1999. From TCR engagement to T cell activation: a kinetic view of T cell behaviour. Cell 96:1
7. A. van der Merwe. 1999. TCR binding to peptide-MHC stabilizes a flexible recognition interface. Immunity 10:357.
8. Altman, J. D., P. A. H. Moss, P. J. R. Goulder, D. H. Barouch, M. G. McHeyzer-Williams, J. I. Bell, A. J. McMichael, and M. M. Davis. 1996. Phenotypic analysis of antigen-specific T lymphocytes. Science 274:94.
9. Kersh, G. J., E. N. Kersh, D. H. Fremont, and P. M. Allen. 1998. High- and low-potency ligands with similar affinities for the TCR: the importance of kinetics in TCR signaling. Immunity 9:817.
10. Valitutti, S., S. Muller, M. Cella, E. Padovan, and A. Lanzavecchia. 1995. Serial triggering of many T-cell receptors by a few peptide-MHC complexes. Nature 375: 148.
11. Garboczi, D. N., D. T. Hung, and D. C. Wiley. 1992. HLA-A2-peptide complexes: refolding and crystallization of molecules expressed in *Escherichia coli* and complexed with single antigenic peptides. Proc. Natl. Acad. Sci. USA 89:3429.
12. Mottez, E., P. Langlade-Demoyen, H. Gournier, F. Martinon, J. Maryanski, P. Kourilsky, and J. P. Abastado. 1995. Cells expressing a major histocompatibility complex class I molecule with a single covalently bound peptide are highly immunogenic. J. Exp. Med. 181:493.
13. Lone, Y-C., Motta, I., Mottez, E., Guilloux, Y., Lim, A., Demay, F., Levraud, J., Kourilsky, P., and Abastado, J., 1998. In virto induction of specific cytotoxic T lymphocyes using recombinant single-chain class I/peptide complexes. *J. Immunother.* 21:283.
14. Mage M G, Lee L, Ribaudo R K, Corr M, Kozlowski S, McHugh L, and Margulies D H 1992. A recombinant, soluble, single-chain class I major histocompatibility complex molecule with biological activity. *Proc Natl Acad Sci USA* 89:10658.
15. Lee L, McHugh L, Ribaudo R K, Kozlowski S, Margulies D H, and Mage M G. 1994. Functional cell surface expression by a recombinant single-chain class I major histocompatibility complex molecule with a cis-active beta 2-microglobulin domain. *Eur. J. Immunol.* 24: 2633.
16. Matsumura, M., Y. Saito, M. R. Jackson, E. S. Song, and P. A. Peterson. 1992. In vitro peptide binding to soluble empty class I major histocompatibility complex molecules isolated from transfected *Drosophila melanogaster* cells. J. Biol. Chem. 267:23589.

17. Stern, L. J., and D. C. Wiley. 1992. The human class II MHC protein HLA-DR1 assembles as empty heterodimers in the absence of antigenic peptide. Cell 68:465.

18. Altman, J. D., P. A. Reay, and M. M. Davis. 1993. Formation of functional Peptide complexes of class II major histocompatibility complex proteins from subunits produced in *Escherichia coli*. Proc. Natl. Acad. Sci. USA 90:10330.

19. Kozono, H., J. White, J. Clements, P. Marrack, and J. Kappler. 1994. Production of soluble MHC class II proteins with covalently bound single peptides. Nature 369:151.

20. White, J., Crawford, F., Fremont, D., Marrack, P., and Kappler, J. 1999. Soluble class I MHC with b-2 microglobulin covalently linked peptides: specific binding to a T-cell hybridoma. *J. Immunol.* 162: 2671.

21. Ignatowicz, L., G. Winslow, J. Bill, J. Kappler, and P. Marrack. 1995. Cell Surface expression of class II MHC proteins bound by a single peptide. J. Immunol. 154:3852.

22. Ignatowicz, L., J. Kappler, and P. Marrack. 1996. The repertoire of T cells shaped by a single MHC/peptide ligand. Cell 84:521.

23. Uger, R. A., and B. H. Barber. 1998. Creating CTL targets with epitope-linked 2-microglobulin constructs. J. Immunol. 160:1598.

24. Rosenberg, S. A. 1997 Cancer vaccines based on the identification of genes encoding cancer regression antigens. *Immunol. Today* 18:175.

25. Van den Eynde, B. and 0. Van der Bruggen. 1997. T-cell-defined tumor antigens. *Curr. Opin. Immunol.* 9: 684.

26. Parkhurst M R, Salgaller M L, Southwood S, Robbins P F, Sette A, Rosenberg S A, and Kawakami, Y. 1996. Improved induction of melanoma-reactive CTL with peptides from the melanoma antigen gp100 modified at HLA-A*0201-binding residues. *J Immunol* 157:2539.

27. Salter, R. D., Howell, D., and Cresswell, P. 1985. Genes regulating HLA class I antigen expression in T-B lymphoblast hybrids. *Immunogenetics* 21:235.

28. Schatz, P. J. 1993. Use of peptide libraries to map the substrate specificity of a peptide-modifying enzyme: a 13 residue consensus peptide specifies biotinylation in *Escherichia coli*. Biotechnology 11:1138.

29. Brumfeld, V., and Werber, M. 1993. Studies of fibronectin and its domains. II Secondary structure and spatial configuration of fibronectin and its domains. *Arch. Biochem. Biophy*. 302:134.

30. Reiter, Y., and Pastan, I. 1998. Recombinant Fv immunotoxins and Fv fragments as novel agents for cancer therapy and diagnosis. *Trends in Biotech.* 16: 513.

31. Bouvier, M., and Wiley, D.C. 1994. Importance of peptide amino and carboxyl termini to the stability of MHC class I molecules. *Science* 265:398.

32. Lee P P, Yee C, Savage P A, Fong L, Brockstedt D, Weber J S, Johnson D, Swetter S, Thompson J, Greenberg P D, Roederer M, and Davis M M, 1999. Characterization of circulating T cells specific for tumor-associated antigens in melanoma patients. *Nat Med* 5:677.

33. Ogg, G. S., X. Jin, S. Bonhoeffer, P. R. Dunbar, M. A. Nowak, S. Monard, J. P. Segal, Y. Cao, S. L. Rowland-Jones, and V. Cerundolo, et al. 1998. Quantitation of HIV-1-specific cytotoxic T lymphocytes and plasma load of viral RNA. *Science* 279:2103.

34. Ogg, G. S., P. R. Dunbar, P. Romero, J. L. Chen, and V. Cerundolo. 1998. High frequency of skin-homing melanocyte-specific cytotoxic T lymphocytes in autoimmune vitiligo. *J. Exp. Med.* 188:1203.

35. Ogg, G. S., and A. J. McMichael. 1998. HLA-peptide tetrameric complexes. *Curr. Opin. Immunol.* 10:393.

36. Dunbar, P. R., J.-L. Chen, D. Chao, N. Rust, H. Teisserenc, G. S. Ogg, P. Romero, P. Weynants, and V. Cerundolo. 1999. Cutting edge: rapid cloning of tumor-specific CTL suitable for adoptive immunotherapy of melanoma. *J. Immunol.* 162:6959.

37. Dunbar, P. R., G. S. Ogg, J. Chen, N. Rust, P. van der Bruggen, and V. Cerundolo. 1998. Direct isolation, phenotyping, and cloning of low-frequencyantigen-specific cytotoxic T lymphocytes from peripheral blood. *Curr. Biol.* 8:413.

38. Bowness, P., R. L. Allen, D. N. Barclay, E. Y. Jones, and A. J. McMichael. 1998. Importance of a conserved TCR J-encoded tyrosine for T cell recognition of an HLA B27/peptide complex. *Eur. J. Immunol.* 28:2704.

39. Schwartz, R. S. 1998. Direct visualization of antigen-specific cytotoxic T cells-Da new insight into immune defenses. *N. Engl. J. Med.* 339:1076.

40. Callan, M. F., L. Tan, N. Annels, G. S. Ogg, J. D. Wilson, C. A. O'Callaghan, N. Steven, A. J. McMichael, and A. B. Rickinson. 1998. Direct visualization of antigen-specific CD8+ T cells during the primary immune response to Epstein-Barr virus in vivo. *J. Exp. Med.* 187:1395.

41. Gallimore, A., A. Glithero, A. Godkin, A. C. Tissot, A. Pluckthun, T. Elliott, H. Hengartner, and R. Zinkernagel. 1998. Induction and exhaustion of lymphocytic choriomeningitis virus-specific cytotoxic T lymphocytes visualized using soluble tetrameric major histocompatibility complex class I-peptide complexes. *J. Exp. Med.* 187:1383.

42. Kuroda, M. J., J. E. Schmitz, D. H. Barouch, A. Craiu, T. M. Allen, A. Sette, D. I. Watkins, M. A. Forman, and N. L. Letvin. 1998. Analysis of Gag-specific Cytotoxic T lymphocytes in simian immunodeficiency virus-infected rhesus monkeys by cell staining with a tetrameric major histocompatibility complex class I-peptide complex. *J. Exp. Med.* 187:1373.

43. Seth, A., I. Ourmanov, M. J. Kuroda, J. E. Schmitz, M. W. Carroll, L. S. Wyatt, B. Moss, M. A. Forman, V. M. Hirsch, and N. L. Letvin. 1998. Recombinant Modified vaccinia virus Ankara-simian immunodeficiency virus gag pol elicits cytotoxic T lymphocytes in rhesus monkeys detected by a major histocompatibility complex class I/peptide tetramer. *Proc. Natl. Acad. Sci. USA* 95:10112.

44. Wilson, J. D., G. S. Ogg, R. L. Allen, P. J. Goulder, A. Kelleher, A. K. Sewell, C. A. O'Callaghan, S. L. Rowland Jones, M. F. Callan, and A. J. McMichael. 1998. Oligoclonal expansions of CD8+ T cells in chronic HIV infection are antigen specific. *J. Exp. Med.* 188:785.

45. Sourdive, D. J., K. Murali-Krishna, J. D. Altman, A. J. Zajac, J. K. Whitmire, C. Pannetier, P. Kourilsky, B. Evavold, A. Sette, and R. Ahmed. 1998. Conserved T cell receptor repertoire in primary and memory CD8 T cell responses to an acute viral infection. *J. Exp. Med.* 188:71.

46. Bousso, P., A. Casrouge, J. D. Altman, M. Haury, J. Kanellopoulos, J. P. Abastado, and P. Kourilsky. 1998. Individual variations in the murine T cell response to a specific peptide reflect variability in naive repertoires. *Immunity* 9:169.

47. Murali-Krishna, K., J. D. Altman, M. Suresh, D. J. Sourdive, A. J. Zajac, J. D. Miller, J. Slansky, and R. Ahmed.

1998. Counting antigen-specific CD8 T cells: a reevaluation of bystander activation during viral infection. *Immunity* 8:177.
48. Romero, P., P. R. Dunbar, D. Valmori, M. Pittet, G. S. Ogg, D. Rimoldi, J. -L. Chen, D. Lienard, J. -C. Cerottini, and V. Cerundolo. 1998. Ex vivo staining of metastatic lymph nodes by class I major histocompatibility complex tetramers reveals high numbers of antigen-experienced tumor-specific cytotoxic T lymphocytes. *J. Exp. Med.* 188:1641.
49. Flynn, K. J., G. T. Belz, J. D. Altman, R. Ahmed, D. L. Woodland, and P. C. Doherty. 1998. Virus-specific CD8+ T cells in primary and secondary influenza pneumonia. *Immunity* 8:683.
50. Yee, C., P. A. Savage, P. P. Lee, M. M. Davis, and P. D. Greenberg. 1999.
51. Isolation of high avidity melanoma-reactive CTL from heterogeneous populations using peptide-MHC tetramers. *J. Immunol.* 162:2227.
52. He, X S, Rehermann, B., Lopez-Labrador F X, Boisvert, J., Cheung, R., Mumm, J., Wedemeyer, H., Berenguer, M., Wtright, T L., Davis, M M and Greenberg H B. 1999 Quantitative analsysis of hepatitis C virus-specific CD8(+) T cells in peripheral blood and liver using peptide-MHC tetramers. *Proc. Natl. Acad. Sci. USA* 96: 5692
53. Gray, M. V., Lawrence, J., Schapiro, J. M., Altman, J. M., Winters, M. A., Crompton, M., Smriti, M., Kundu, M., Davis, M. M., And Merigan. T. C. 1999. Frequency of Class I HLA-Restricted Anti-HIV CD8+ T Cells in Individuals Receiving Highly Active Antiretroviral Therapy (HAART). *J. Immunol* 162: 1780.
54. Bieganowska, K., Hullsberg, p., Buckle, j. b., Lim, D., Greten, T. F., Schneck, J., Altman, J. D., Jacobson, S., Ledis, S. L., Hanchard, B., Chin, J., Morgan, O., Roth, P. A., and Hafler D. A. Direct Analysis of Viral-Specific CD8+ T Cells with Soluble HLA-A2/Tax11-19 Tetramer Complexes in Patients with Human T Cell Lymphotropic Virus-Associated Myelopathy *J. Immunol* 162:1765-1771
55. De Haard, H., Henderikx, P., and Hoogenboom, H. R., 1998. Creating and Engineering human antibodies for immunotherapy. *Adv. Drug. Delv. Rev.* 31: 5.
56. Andersen, P. S., Stryhn, A., Hansen, B. E., Fugger, L. & Engberg, J. (1996) A recombinant antibody with the antigen specific, major histocompetibibity complex-restricted specificity of T cells. *Proc. Natl. Acad. Sci. (USA)* 93:1820.
57. Reiter, Y., DiCarlo, A., Engberg, J., and Pastan, I. (1997) Peptide-specific killing of antigen-presenting cells by a recombinant antibody-toxin fusion protein targeted to MHC/peptide class I complexes with T-cell receptor-like specificity. *Proc. Natl. Acad. Sci. USA* 94: 4631.

What is claimed is:

1. A plurality of complexes each being composed of an antigenic peptide being capable of binding a human MHC class I, and a chimeric polypeptide which comprises a functional human β-2 microglobulin translationally fused upstream of a functional human MHC class I heavy chain, wherein all of said plurality of complexes are identical and recognizable by one CTL clone.

2. The plurality of complexes of claim 1, wherein said chimeric polypeptide further comprises a linker peptide being interposed between said functional human β-2 microglobulin and said functional human MHC class I heavy chain.

3. The plurality of complexes of claim 1, wherein said antigenic peptide is covalently linked to said chimeric polypeptide.

4. A bacterial inclusion body comprising a chimeric polypeptide which comprises a functional human β-2 microglobulin translationally fused to a functional human MHC class I heavy chain.

* * * * *